US009428737B1

(12) United States Patent
Gaucher

(10) Patent No.: US 9,428,737 B1
(45) Date of Patent: Aug. 30, 2016

(54) TAQ POLYMERASE SEQUENCES USEFUL FOR INCORPORATING ANALOGS OF NUCLEOSIDE TRIPHOSPHATES

(76) Inventor: Eric Gaucher, Atlanta, GA (US)

( * ) Notice: Subject to any disclaimer, the term of this patent is extended or adjusted under 35 U.S.C. 154(b) by 535 days.

(21) Appl. No.: 12/655,931

(22) Filed: Jan. 11, 2010

(51) Int. Cl.
*C12N 9/12* (2006.01)
(52) U.S. Cl.
CPC .................... *C12N 9/1252* (2013.01)
(58) Field of Classification Search
None
See application file for complete search history.

(56) References Cited

U.S. PATENT DOCUMENTS

| 5,302,509 | A | 4/1994 | Cheeseman |
| 5,614,365 | A * | 3/1997 | Tabor et al. ............... 435/6.12 |
| 6,228,628 | B1 * | 5/2001 | Gelfand et al. ............. 435/194 |

OTHER PUBLICATIONS

Ngo et al. In the Protein Folding Problem and Tertiary Structure Prediction, 1994, Merz et al. (ed.), Birkhauser, Boston, MA, pp. 433 and 492-495.*
Parker et al., BioTechniques vol. 21, pp. 694-699, 1999.*
Axelrod, V. D., Vartikyan, R. M., Aivazashvili, V. A., Beabealashvili, R. S. (1978) Specific termination of RNA polymerase synthesis as a method of RNA and DNA sequencing. Nucleic Acids Res. 5, 3549-3563.
Bateman, A., Coin, L., Durbin, R., et al. (2004) The Pfam protein families database. Nucleic Acids Res, 32, D138-41.
Burgess, K., Gibbs, R. A., Metzker, M. L., Raghavachari, R. (1994) Synthesis of an oxyamide linked nucleotide dimer and incorporation into antisense oligonucleotide sequences. J. Chem. Soc. Chem. Commun. 8, 915-916.
Canard, B., Cardona, B., Sarfati, R. S. (1995) Catalytic editing properties of DNA polymerases. Proc. Natl. Acad. Sci. USA 92, 10859-10863.
Cook, P. D., Sanghvi, Y. S. (1994) Preparation of antisense heteroatomic oligonucleotide analogs. PCT Int. Appl. 90 pp.
De Clercq, E., Inoue, I., Kondo, K. (1990) Preparation of 3-O-amino-2'-deoxyribonucleoside derivatives as antiviral agents for human retrovirus, particularly human immunodeficiency virus. Eur. Pat. Appl. 14 pp.
Evans, S. J., Fogg, M. J., Mamone, A., Davis, M., Pearl, L.H., Connolly, B.A. (2000) Improving dideoxynucleotide-triphosphate utilisation by the hyper-thermophilic DNA polymerase from the archaeon Pyrococcus furiosus. Nucl. Acids Res. 28, 1059-1066.
Gardner, F., Jack, W. E. (1999) Determinants of nucleotide sugar recognition in archaeon DNA polymerase. Nucl. Acids Res. 27, 2545-2553.
Ghadessy, F. J., Ong, J. L., Holliger, P. (2001) Directed evolution of polymerase function by compartmentalized self-replication. Proc. Natl. Acad. Sci. USA 98, 4552-4557.
Hendrickson, C., Devine, K., Benner, S. A. (2004) Probing the necessity of minor groove interactions with three DNA polymerase families using 3-deaza-2'-deoxyadenosine 5'-triphosphate. Nucl. Acids Res. 32, 2241-2250.

Henry, A. A. & Romesberg, F. E. (2005) The evolution of DNA polymerases with novel activities. Curr Opin Biotechnol, 16, 370-7.
Horlacher, J., Hottiger, M., Podust, V. N., Hubscher, U. & Benner, S. A. (1995) Recognition by viral and cellular DNA polymerases of nucleosides bearing bases with nonstandard hydrogen bonding patterns. Proc Natl Acad Sci U S A, 92, 6329-33.
Hyman, E. D. (1988) A new method of sequencing DNA. Anal. Biochem. 174, 423-436.
Ireland, R. E., Varney, M. D. (1986) Approach to the total synthesis of chlorothricolide-synthesis of (+/−)-19.20-dihydro-24-O-methylchlorothricolide, methyl-ester, ethyl carbonate. J. Org. Chem. 51, 635-648.
Ju, J., Glazer, A. N., Mathies, P. A. (1996) Cassette labeling for facile construction of energy transfer fluorescent primers. Nucleic Acids Res. 24, 1144-1148.
Ju, J., Ruan, C., Fuller, C. W., Glazer, A. N., Mathies, R. A. (1995) Energy transfer fluorescent dye-labeled primers for DNA sequencing and analysis. Proc. Natl. Acad. Sci. USA 92, 4347-4351.
Kamal, A., Laxman, E., Rao, N. V. (1999) A mild and rapid regeneration of alcohols from their allylic ethers by chlorotrimethylsilane/sodium iodide. Tetrahedron Lett. 40, 371-372.
Leal, N. A.. Sukeda, M. & Benner, S. A. (2006) Dynamic assembly of primers on nucleic acid templates. Nucleic Acids Res, 34, 4702-10.
Metzker, M. L., Raghavachari, R., Richards, S., Jacutin, S. E., Civitello, A., Burgess, K., Gibbs, R. A. (1994) Termination of DNA synthesis by novel 3'-modified-deoxyribonucleoside 5'-triphosphates. Nucleic Acids Res. 22, 4259-4267.
Mitra, R. D., Shendure, J., Olejnik, J., Olejnik, E. K., Church, G. M. (2003) Fluorescent in situ sequencing on polymerase colonies. Anal. Biochem. 320, 55-6.
Ronaghi, M., Uhlen, M., Nyren, P. (1998) a sequencing method based on real-time pyrophosphate. Science 281, 364-365.
Roses, A. (2000) Pharmacogenetics and the practice of medicine. Nature 405, 857-865.

(Continued)

*Primary Examiner* — Richard Hutson

(57) ABSTRACT

This patent applications concerns compositions of matter that are DNA polymerases, where those polymerases have had one or more of their amino acids replaced at sites chosen by an analysis of patterns of conservation and replacement within homologous protein sequences. Disclosed here are sites within Family A DNA polymerases where amino acid replacement creates polymerases having utility, in an example where DNA nucleotides are incorporated having modified or unnatural nucleobases, and/or nucleotides whose sugar is unnatural or derivatized, including 3'-O-amino-2'-deoxyribonucleoside triphosphates. The claimed compositions include polymerases that hold amino acid replacements at claimed sites in Taq polymerase, and are prepared by site-directed mutagenesis that modifies a gene encoding a parent Taq gene (natural or already mutated) to change the codon encoding the amino acid at the claimed site, giving a variant gene that encodes a Taq polymerase protein that has a different amino acid at the claimed site.

1 Claim, 6 Drawing Sheets

(56) References Cited

OTHER PUBLICATIONS

Salas-Solano, O., Carrilho, E., Kotler, L., Miller, A. W., Goetzinger, W., Sosic, Z., Karger, B. L. (1998) Routine DNA sequencing of 1000 bases in less than one hour by capillary electrophoresis with replaceable linear polyacrylamide solutions. Anal. Chem. 70, 3996-4003.

Seo, T.S., Bai, X., Ruparel, H., Li, Z., Turro, N. J., Ju, J. (2004). Photocleavable fluorescent nucleotides for DNA sequencing on a chip constructed by site-specific coupling chemistry. Proc. Natl. Acad. Sci. USA 101, 5488-5493.

Sismour, A. M., Lutz, S., Park, J. H., et al. (2004) PCR amplification of DNA containing non-standard base pairs by variants of reverse transcriptase from Human Immunodeficiency Virus-1. Nucleic Acids Research, 32, 728-735.

Smith, L. M., Sanders, J. Z., Kaiser, R. J., Hughes, P., Dodd, C., Connell, C. R., Heiner, C., Kent, S. B. H., Hood, L. E. (1986) Fluorescence detection in automated DNA sequencing analysis. Nature 321, 674-679.

Tabor, S., Richardson, C. C. (1987) DNA sequence analysis with a modified bacteriophage T7 DNA polymerase. Proc. Natl. Acad. Sci. USA 84, 4767-4771.

Tabor, S., Richardson, C. C. (1995) A single residue in DNA polymerases of the *Escherichia coli* DNA polymerase I family is critical for distinguishing between deoxy- and dideoxyribonucleotides. Proc. Natl. Acad. Sci. USA 92, 6339-6343.

Welch, M. B., Burgess, K. (1999) Synthesis of fluorescent, photolabile 3'-O-protected nucleoside triphosphates for the base addition sequencing scheme. Nucleosides Nucleotides 18,197-201.

Kheterpal, I., Scherer, J.R., Clark, S.M., Radhakrishnan, A., Ju, J.Y., Ginther, C.L., Sensabaugh, G.F., Mathies, R.A., (1996) DNA sequencing using a four-color confocal fluorescence capillary array scanner. Electrophoresis 17, 1852-1859.

Kondo, K., Ogiku, T., Inoue, I. (1985) Synthesis of 5'(3') -O-amino nucleosides. Symp. Nucleic Acids Chem. 16, 93-96.

\* cited by examiner

FIG. 1A SEQ ID NO:1

```
         10         20         30         40         50         60
          |          |          |          |          |          |
MRGMLPLFEP NGRVLIVDGH HLAYRTFHAL KGLTTSRGEP VQAVYGFAKS LLKALKEDGD 70         80         90        100        110        120
          |          |          |          |          |          |
AVIVVFDAKA PSFRHEAYGG YKAGRAPTPE DFPRQLALIK ELVPLLGLAR LEVPGYEADD 130        140        150        160        170        180
          |          |          |          |          |          |
VLASLAKKAE KEGYEVRLIT ADKDLYQLLS DRIHVLHPEG YLITPAWLWE KYGLRPIQWA 190        200        210        220        230        240
          |          |          |          |          |          |
DYRALTGDES DNLPGVKGIG EKTARRILEE WGSLEALLKN LDRIKEAIRE KIAHMDDLK 250        260        270        280        290        300
          |          |          |          |          |          |
LSWDLAKVRT DLPLEVDFAK RPEEDERLR AFLERLEFGS LLHEFGLLES EKALEEAPWP 310        320        330        340        350        360
          |          |          |          |          |          |
PPEGAFVGFV LSRKEPMWAD LLALAAARGG RVHRAPEPYK ALRDLKEARG LLANDLSVLA 370        380        390        400        410        420
          |          |          |          |          |          |
LREGLGLPPG DDPMLLAYLL DPSNTTPEGV ARRYGGEWTE EAGERAALSE RLFANLWGRL
```

FIG. 1B SEQ ID NO:1

```
         430        440        450        460        470        480
          |          |          |          |          |          |
    EQEERLIWLY REVERPLSAV LARMEATGVR LDVAYLRALS LEVAEKIARL EAEVEFLAGH 490        500        510        520        530        540
          |          |          |          |          |          |
    PFMLNSRDQL ERVLFDRIGL PAIGKTEKTG KRSTSAAVLE ALREAHPIVE KILQYRELTK 550        560        570        580        590        600
          |          |          |          |          |          |
    LKSTYIDPLF DLIHPRTGRL HTRPNGTATA TGRLSSSDPN LQNIPVRTPL GQRIRRAETA 610        620        630        640        650        660
          |          |          |          |          |          |
    EEGMLLIVALD YSQLELRVLA HLSGENLIR VFQEGRDIHT ETASWMEGVP REAVDPLMRR 670        680        690        700        710        720
          |          |          |          |          |          |
    AAKTTNFGVL YGMSAHRISQ ELAIPVEEAQ AFTERYFQSF PNVRAWTEKT LEEGRRRGYV 730        740        750        760        770        780
          |          |          |          |          |          |
    ETLEVGRRRYV PDLEARVLSV REAAEHRMAFN MPVQGTAADL MKLAMVKLFP RLEERGARML 790        800        810        820        830
          |          |          |          |          |
    LQVHDEIVLE APKERARAVA RLAKEVMEGV YPLAVPLEVE VGIGEDWLSA KE
```

FIG. 2A

```
DPO1_THEAQ/451-830    LDVAVLRALSLEVAEE.IARLEAEVTSLAGHFFNLMSRDQERVLFDELGLPAIGKTEKT.GERSTSAAVLEALRE..AH
DPOG1_HUMAN/730-1182  PSYHHGNGPYMDVDIPGCW..FFKLPHEDGMSCNVGSPPAKDFLPKMEDETLQAGPGGAS.GPPALEINKMISHWRN.AH
DPOG_YEAST/531-939    VSQEREBIRTHNLGLQ.CTGVLEKVFPHNGFTFNCTNLLTKSYNHFFEKGVLKSESELAH..QALQINSGSYWMS.AR
DPO1_DEIRA/576-955    VDSDFLAQTLSLQAGVR.LADLESQLHEYAGEEPHIRSPKQLETVLYDKLELASSKKTKLI.GQRSTAVSALEPLRD..AH
DPO1_ECOLI/547-927    IDFKVLWNSEELTER.LAELEKKAHETAGEEPNLSSTRQLQTILFEKQGIKPLKKTFG..GAPSTSBEVLEEIAL..DY
DPO1_HAEIN/550-929    IDSDALFMQSMEIASR.LPALEKQAYALASQPFNLASTKQLQEHLFDKLELPVLQKTPK..VLKKTK.TGYSTSADVLERLAP..HH
DPO1_BACST/495-875    VDTKRLEQMGAELTEQ.LQAVERRIYELAGQEFNINSPRQLGTVLFDKLQP..VLKKTK.TGYSTSADVLERLAP..HH
DPO1_STRR6/494-876    VKKETLLEMQAENELV.IEKLTQEIYELAGEEKFVNSPKQLGVLLEEKLGLP.LEYTEKTGYSTAVDVLERLAP.IA
DPO1_MYCTU/522-902    VDLPMLFELQSQFGDQ.IRDAEAAYGVIGKQINLGSPKQLQVLFDELGMF..KTARTK.TGYTTDADALQSLPDKTGE
DPO1_BPSP1/474-870    KSANRTPEQQDRFKKY...KKYDPSKGGEKHMFGSTRQLGELLFERMGLETVLFTDK..GAPSTNDDSLKPNGS..QS
DPO1_BPML5/238-590    LDVEYSPSLAEKWLADQEVWEALAFTEYGVEKVNSTEDLAEG...LEEMGVKITGRPEE..GKRQVNAALLDKLVED.GN
DPO1_BPT7/308-703     EGREIPCELDTREYVAG......APYTPVEBVVEMPSSRDHIQKRLQEAGWVT.TKYTEK..CAPVVDEVLEGVRVDPPE

DPO1_THEAQ/451-830    PIVEKRILQY.....RELTKLKSTYIDPLPDLIHPFTGRLHTRFNQTATATGRLSSDPWLQMIPVST.......PLGQRIRR
DPOG1_HUMAN/730-1182  KRISSQMVV..WIPRSALPRAVIRHPDYDEEGLYGAILPQVVTAGTITRRAVEPTWLTASNARPD......RVGSELKA
DPOG_YEAST/531-939    ERIQSQFVPSCKFPNEFQSLSAKSSLNNEKTNDLAIIPKIVPMCTTTRRAVENAWLTASNAKAN......RIGSELET
DPO1_DEIRA/576-955    PITPLVEF.....RELDKIRGTYLEPIPNLVNPHTGRLHTTFAQTAVATGRLSSLNPHLQMIPIRS......ELGREIRK
DPO1_ECOLI/547-927    PLPKVILEY....RCLAKILKSTYTDKLPLMTNPKTGRVEHTSYHQAVTAHGRLSSTDPNLQMTPVRN......ZEGRRIRQ
DPO1_HAEIN/550-929    RLPKILVKH....RGISKIIKSTYTDKLPQMVNSQTGKVHTSYHQAVTATGRLSSDPNLQMIPKN......EEGSHIRQ
DPO1_BACST/495-875    EIVEHIHY.....RQLGKLQSTYIEGLLKVVHPVTGKLVHTMENQALTQTGRLSVEPMLQMIPIRL......EEGREIRQ
DPO1_STRR6/494-876    PIVKKILDY....RQIAKIQSTYVTGLQTV.VDGSLLQAVA.ADGRIHTFPNQTIAATGRLSTEPNLQMIPIRT......DAGRRIRD
DPO1_MYCTU/522-902    PFLQHLLAH....RDVTRLKVT.VDGSLLQAVA.ADGRIHTFPNQTIAATGRLSTEPNLQMIPIRT......DAGRRIRD
DPO1_BPSP1/474-870    DFVKLMEE....EHAMSLYNMFVSKLSLMID.PDMIVHFSINIRCTVTGRLSSNEFWAQEFFRKVNPTTLFQVNFEIKK
DPO1_BPML5/238-590    ELAIAQEA...KKIGKWRKTWVQKFIDTEQ.SEDNCHTENPLQAKTSRMSITGIPAQTLPSSD......WIVRE
DPO1_BPT7/308-703     RQAAIDLINEYLMIQKBIGQSAKGDKAWLRYVAEDKIBGSVNPNGAVPGRATHAFPNLAQFGVR......SPYGEQCEA
```

FIG. 2B

```
DPO1_THEAQ/451-830      AFIAEEG..WLLVALDYSQIEIRVLAHLSGDENLIRVFQEGRDIHTETASWMFGVPREA....VDPLMRRAAKTINFGVL
DPOG1_HUMAN/730-1182    MVQAPPG..YTLVGADVPSKQELWIAAVLGDAHFAGMKGCTAHGWMTLQCRKSRGTDLHSKPATTVGISREHAKIFNYGKI
DPOG_YEAST/531-939      QVKAFPG..YCFVGADVGSEELWIASLVGDSIFN..VHGGTAICMMCLECTKNEGTDLHTKTAQILGCSRNEAKIFNYGFI
DPO1_DEIRA/576-955      CFIAEPG..FTLIAADYSQIEIRILAHIADDPLMQQAFVEGADIHRATAAQVLGLDEAT....VDANQERAAKTVNFGVL
DPO1_ECOLI/547-927      AFIAPED..YVIVSADYSQIELRIMAHLSRDKGLLTAEAEGKDIHRATAEAEVFGLPLET....VTSEQRRSAKAINEGLI
DPO1_HAEIN/550-929      AFIAREG..YSIVAADYSQIELRHMAHLSHQGLINAFSGQKDIHKSTAAHFGVSLDE....VTSEQRRNAKAINFGLI
DPO1_BACST/495-875      AFVPSEPD..WLIEAABYSQIEIRVLAHIAEDINLIEAFRGLDIHTKTAMDIFHYSEED....VTAMMRQAKAVNFGJV
DPO1_STRR6/494-876      AFVEMRD..SVLLSSDYSQIEIRVIAHISKMEHLIKAPQEGADIHTSTAMKVTGERPD....NVTAMERRNAKAVNFGVV
DPO1_MYCTU/522-902      AFVVGDSY..ARLMTADYSQIEMRIMAGLSGDEGLIEAFNTGEDLHSFVASRAEGVPIDE....VTGELRRPVKAMSYGLA
DPO1_BPSP1/474-870      MFNSKFGMGGVIVQPDYSQLEIRILVCYSRPYTIDLYRSGADLHKAVASGAFGVAIEE....VSKDGRTASKIQFGHV
DPO1_BPML5/238-590      CFLAEPG..DVMASVDYCAQELRVLAALSGDRMMIEAFERGADLHQMZ.AD......AAQVPFKVGKTANFGKV
DPO1_BPT7/308-703       AFGAEHHLDGTTGKPVGAGIDASGLELPCLAHTMARETMGGEYAHEIILNGDIHTKNQIA....AELPTRDNAKTFIYGFL

DPO1_THEAQ/451-830      YGMSAHRLSQELA....IPYEEAQAFIERYFQSEPK.................VRAWIEKTL
DPOG1_HUMAN/730-1182    YGAGQPPAERLLMQPNHRLTQQEAAEKAAQQMYAATKGLRWYRLSDEGEWLVRELNLPVDKTEGGWISLQDIRKYQRETAR
DPOG_YEAST/531-939      YGACAKFASQLLKRFNPSLIDEETKKIANRLYEWTKG.................KTKRSKLF
DPO1_DEIRA/576-955      YGMSAHRLSNDLG.....IPYAEAATFEIYFATYPG.................IRRYINHTL
DPO1_ECOLI/547-927      YGMSAFGLARQLN.....IPRKEAQKYMDLYFERYPG.................VLEYMERTR
DPO1_HAEIN/550-929      YGMSAFGLSRQLG.....ISPADRQKYMDLYFQRYPS.................VQQFMTDER
DPO1_BACST/495-875      YGISDYGLAQNLN.....ITTKEAAEFIERYFASFPG.................VKQYMONIV
DPO1_STRR6/494-876      YGISDFGLSNNLG.....ISREEAKAYIDTYFERFPG.................IKNYMPEVV
DPO1_MYCTU/522-902      YGLSAYGLSQQLK.....ISTEEANEQMDAYFAREGG.................VRPYLRAVV
DPO1_BPSP1/474-870      YQESARGLSEDIRAEGITMSEEBRCEIFIRKVYKREPK.................VSRKWPDTK
DPO1_BPML5/238-590      YGGGAKALABAVG.....ISIPVAKRVHEAFSATYPG.................VEHLSKKLA
DPO1_BPT7/308-703       VGAGDEKIGQIVG.....AGKERGAELKKKPLENTPA.................IAALRESIQ
```

FIG. 2C

```
DPO1_THEAQ/451-830      E..........EERRKGYVETLFGRRR....VYPDLEAR...VKSVREAAERM.......APNMPVQGTAADLMKLAM
DPOG_HUMAN/730-1182     KSQMKKWKVVLAERAWKGGTESEMFNKLESIATSDIPRTPVLGCCISRALFSAVQE.EMTSRVNWTVCQSSAVDYLHLML
DPOG_YEAST/531-939      K..........KFWYGGSESILFMKLESIAEQETPKTPVLEGKTTYSLMKKNLRANSFLPSRINWAIQSSGVDYLHLLC
DPO1_DEIRA/576-955      D..........FGRTHGYVETLGRRR....YVPGLSSR...MRVQREAEERL.......AYNMPIQGTAADIMKLAM
DPO1_ECOLI/547-927      A..........QAKEQGYVETLFGRPL....YLPDIKSS...MGARRAAERA.......AINAPMQGTAADIIKRAM
DPO1_HAEIN/550-929      E..........KARAQGYVETLFGPRL....YLPDINSS...MAMRRKGAEBRV.....AINAPMQGTAADIIKRAM
DPO1_BACST/495-875      Q..........BAKQRGYVTTLLHRRR....YLPDTSR....MENVRSFARRT......AMNTPIQCSAADILKKAM
DPO1_STRR6/494-876      R..........BARDKGYVETLFKRKR....ELPDINSR...MEMIRGFAERT......AINSFLQGSAADLKIAM
DPO1_MYCTU/522-902      E..........BARDGYTSTVLGKRR....YLPELDSS....MRQVEAARRA.......AINAPLQGSAADIKVAM
DPO1_BPSP1/474-870      K..........BVKDISTVETLFGATR....MLPDIDSID..QSKANEAERQ.......AVNTPIQGTGSDCTLMSL
DPO1_BPML5/238-590      M..........EAGRNGYIVNAMSERL....PVDSSR..................... ALNYMIQSSRDVTCAAL
DPO1_BPT7/308-703       QTLVE......SSOWVAGEQQVKKRR....WIKGLDGR.... KVHVRSPHA.......ALNTLLQSAGALICKLWI

DPO1_THEAQ/451-830      VKLFPPLEEM..GA......RMLLQVHDELVLEAPKER..ABAVARLAKEVMEGVYPL......AVPLEVEVGIG.ED
DPOG_HUMAN/730-1182     VAMKWLFEEAIDG......RFCISIHDEVRYLVRBEDRYRAALALQITNLLTRCMEA......YKLGLNLPQS.VA
DPOG_YEAST/531-939      CSMEYITKKYMLEA......RLCISIHDEIRFLVSEKDKYRAAMALQISNIWTRAMFC.....QQMSINBLFQN.CA
DPO1_DEIRA/576-955      VQLDPQLDAJ..GA......RMLLQVHDELLIEAPLDK..ABQVAALTKKVMENVYQL.....RVPLAVEVGTG.PN
DPO1_ECOLI/547-927      IAVDAWLQAEQPRV......RMIMQVHDELVEVEKDD..VDAVAKQIHQLMENCTRL.....DVPLLVEVGSG.EN
DPO1_HAEIN/550-929      IKLDEVIRHD.PDI......EMIMQVHDELVEFVRSEK..VAFFREQIKQHMEAAEL.....VVPLIVEVGVG.QN
DPO1_BACST/495-875      IDLSVRLEERLQA.......RLLLQVHDELILEAPKEE..IERLCNLVPEVMEQAVTL....RVPLKVDYHIG.PT
DPO1_STRR6/494-876      IQLTKALVAGGYQT......KMLLQVHDEIVLEVKSE...LVEMRKLVKQTREEAIQL....SVPLIADENBG.AT
DPO1_MYCTU/522-902      IQVDKALNEAQLAS......BMLLQVHDELLFEIAPGE..RERVEALVRDRMGGAYPL....DVPLEVSVGIG.RS
DPO1_BPSP1/474-870      ILINQWLRESGLRS......RICITVHDSIVLDCPKDE..VLEVAKKVKHTEMLGEYMEFYKFLGQVPILSBMEIG.RN
DPO1_BPML5/238-590      IRLHEAGYTP..........YLRLPIHDEIVASLFASE..ABRAAABICHLMQEQMGP...........VLVGTDEPVGKRS
DPO1_BPT7/308-703       IKTEEMLVERGLKHGWMGDEAYMANWHDEIQVGCRTEE..IAQVIETAQEAMRWVGDHWN..FRCLLDTEKMG.PN
```

FIG. 2D

| | | |
|---|---|---|
| DPO1_THEAQ/451-830 | WLSA | SEQ ID NO:1 |
| DPO3_HUMAN/730-1132 | FFSA | SEQ ID NO:9 |
| DPOG_YEAST/531-939 | FFSQ | SEQ ID NO:8 |
| DPO1_DEIRA/576-955 | WFDT | SEQ ID NO:4 |
| DPO1_ECOLI/547-927 | WDQA | SEQ ID NO:2 |
| DPO1_HAEIN/550-929 | WDEA | SEQ ID NO:5 |
| DPO1_BACST/495-875 | WYDA | SEQ ID NO:7 |
| DPO1_STRRG/494-876 | WYEA | SEQ ID NO:3 |
| DPO1_MYCTU/522-902 | WDAA | SEQ ID NO:6 |
| DPO1_BFSPI/474-870 | YGDA | SEQ ID NO:11 |
| DPO1_BPML5/238-590 | WGSL | SEQ ID NO:10 |
| DPO1_BPT7/308-703 | WAIC | SEQ ID NO:12 |

TAQ POLYMERASE SEQUENCES USEFUL FOR INCORPORATING ANALOGS OF NUCLEOSIDE TRIPHOSPHATES

STATEMENT OF FEDERALLY SPONSORED RESEARCH

The Federal government may have certain rights through its sponsorship of this research under NIH grant R21HG003581

SEQUENCE LISTING

A sequence listing is appended, on a compact list and printable form (31 pp). Both forms are identical

FIELD

This invention relates to the field of biotechnology, more specifically that part of this field that concerns the enzymatic synthesis of DNA using DNA polymerases, and most specifically the enzymatic synthesis of DNA that involves the incorporation of analogs of natural nucleoside triphosphates

BACKGROUND

The ability to sequence and re-sequence (a term that describes the sequencing of a new genome while making reference to the genome of a closely related organism, generally of the same species) deoxyribonucleic acid (DNA) has the potential for revolutionizing biology and medicine. The ability to re-sequence segments of the genome of individual humans will enable the personalization of medicine, as the genetic differences between individuals carries information about how those individuals will respond differently to similar treatments [Ros00].

Most DNA sequencing is done today using capillary array DNA sequencers that detect fluorescent dyes appended to the 5- or 7-positions of pyrimidine or 7-deazapurine nucleobases attached to dideoxynucleotide analogs [Smi86] [Ju95][Ju96][Khe96][Sal98]. These analogs, present as a small fraction of the total nucleotide triphosphates, stochastically and irreversibly terminate an elongating DNA chain, because they lack a 3'-OH group. Mutant polymerases have improved the uniformity and efficiency of termination, improving the quality of sequencing data [Tab87][Tab95].

While this sequencing strategy has created the "postgenomic world", it has well known limitations. Primary among them is that it is difficult to multiplex; each sequence must be determined separately on a separate capillary. Further, it is not exquisitely sensitive; it cannot determine the sequence of a small number of molecules, and is insufficiently sensitive to sequence a single molecule of DNA. Further, the irreversibly terminated elongating DNA strands cannot be cloned. Further, the irreversible termination does not introduce a moiety into the oligonucleotide that can be later used to recover the product strand.

In part to enhance multiplexing, in part for other reasons, sequencing by synthesis without using electrophoresis was proposed as a strategy in 1988 [Hym88]. Generically, the strategy involves detecting the identity of each nucleotide at the same time as it is incorporated into the growing strand of DNA in a polymerase-catalyzed reaction. A variety of architectures have been proposed for performing "sequencing by synthesis" [Che94][Met94]. These differ in the way that the nature of the nucleotide that was just incorporated in each step of the synthesis is determined. They also differ by the tactic used to prevent the addition of the following nucleotide until the identity of the nucleotide that was just incorporated had been determined.

For example, in the pyrosequencing architecture [Ron98], a "minus" strategy is used to look at single nucleotide incorporations. Here, only one of the four natural nucleoside triphosphates is incubated in the reaction at any one time. Detection is based on the release of pyrophosphate during the DNA polymerase reaction, indicating the addition to the elongating chain of the added triphosphate, or the absence of the release of pyrophosphate. The pyrophosphate is detected through its conversion to adenosine triphosphate (ATP) by sulfurylase, which then generates visible light in the presence of firefly luciferase.

The limitations of this procedure are also well known in the art. First, the amount of pyrophosphate must be quantitated to distinguish between the addition of a single nucleotide of the type added, or of several in a "homosequence run". While this is readily done for runs of one, two, or three nucleotides, it becomes progressively more difficult as the runs become longer. Further, each of the four nucleoside triphosphates must be added separately. Polymerases are well known to misincorporate when they are not presented with the complementing triphosphate. This creates undesired termination, in many cases, or "ragged ends" in others.

Another architecture uses a polymerase to direct the incorporation, in a template-directed polymerization step, of a nucleoside triphosphate or thiotriphosphate (which is useful in certain architectures) having its 3'-hydroxyl group blocked by a removable protecting (or blocking) group. This blocking group prevents the polymerase from adding additional nucleotides until the blocking group is removed. In practice, this provides an arbitrarily long time to determine the nature of the added nucleotide.

A frequent proposal for this architecture is to place different distinctive tags on the four nucleobases. These tags may be distinctively colored fluorescent groups, although other tags have been proposed. Then, after the blocked nucleotide is incorporated, the nature of the nucleotide incorporated is determined by reading the fluorescence that comes from the tag. After this is done, the 3'-protecting group is removed to generate a 3'-OH group at the 3'-end of the elongating primer, the tag is removed, and the next cycle of sequencing is initiated. In this architecture, template-directed polymerization is done using a DNA polymerase or, conceivably, a reverse transcriptase [Mit03].

When the output is fluorescence, this implementation of the strategy requires:

(a) Four analogues of dATP, dTTP, dGTP, and dCTP, each carrying a fluorescent dye with a different color, with the 3'-end blocked so that elongation is not possible.

(b) The four analogues must be efficiently incorporated, to allow the elongation reaction to be completed before undesired reactions occur, and to avoid ragged ends arising from incomplete incorporation. For single molecule sequencing, failure to incorporate is still undesirable, as a cycle of sequence collection is missed.

(c) The incorporation must be faithful. Mismatched incorporation, if not corrected by proofreading, will lead to the loss of strands if the polymerase does not extend efficiently a terminal mismatch. This will gradually erode the intensity of the signal, and may generate "out of phase" signals that confuse the reading of the output downstream. Large numbers of errors will, of course, confuse the primary signal. For single molecule sequencing, misincorporation may well mean the end of a read.

(d) The dye and the group blocking the 3'-OH group need to be removed with high yield to allow the incorporation of the next nucleotide of the next nucleotide to proceed. Less than 99% completion for each cycle (and incompletion) will gradually erode the intensity of the signal, and may generate "out of phase" signals that confuse the reading of the output downstream. For single molecule sequencing, failure to cleave the 3'-OH blocking group may not create a decisive error, but it can lose a cycle of sequence data collection.

(e) The growing strand of DNA should survive the washing, detecting and cleaving processes. While reannealing is possible, we preferably would like conditions that allow the DNA primer and template to remain annealed.

It their most ambitious forms, sequencing-by-synthesis architectures would use the same nucleoside modification to block the 3'-end of the DNA and to introduce the fluorescent tag [Wel99]. For example, if a fluorescent tag is attached to the 3'-position via an ester linkage, replacing the hydrogen atom of the 3'-OH group of the nucleoside triphosphate, extension following incorporation would not be possible (there is no free 3'-OH group). This would give time to read the color of the fluorescent label, determining the nature of the nucleotide added. Then, the 3'-O acyl group could be removed by treatment with a mild nucleophile (such as hydroxylamine) under mild conditions (pH<10) to regenerate a free 3'-hydroxyl group, preparing the DNA for the next cycle.

The difficulty in implementing this elegant approach is the polymerases themselves. Any tag that fluoresces in a useful region of the electromagnetic spectrum must be large, on the order of 1 nm. Crystal structures of polymerases show that the 3'-position in the deoxyribose unit is close to amino acid residues in the active site of the polymerase, and do not offer the incoming triphosphate the space to accommodate a tag of that size. The structure of the ternary complexes of rat DNA polymerase beta, a DNA template-primer, and dideoxycytidine triphosphate (ddCTP) from the Kraut laboratory, as well as a variety of structures for other polymerases from other sources solved in other laboratories, illustrates this fact. The polymerase, therefore, is not likely to be able to handle substituents having a tag of this size at the 3'-position. Indeed, polymerases do not work well with any modification of the 3'-OH group of the incoming triphosphate. For example, to accept even 2',3'-dideoxynucleoside analogues (where the 3'-moiety is smaller than in the natural nucleoside), mutated polymerases are often beneficial.

Ju et al., in U.S. Pat. No. 6,664,079, noted these problems as they outlined a proposal for sequencing by synthesis based on 3'-OH blocking groups. Therefore, they argued that the prior art had not been enabled, even though it specified many details of an architecture for sequencing by synthesis. They suggested that this problem might be addressed using nucleotide analogues where the tag, such as a fluorescent dye or a mass tag, is linked through a cleavable linker to the nucleotide base or an analogue of the nucleotide base, such as to the 5-position of the pyrimidines (T and C) and to the 7-position of the purines (G and A). Bulky substituents are known to be accepted at this position; indeed, these are the sites that carry the fluorescent tags in classical dideoxy sequencing. According to Ju et al., tags at this position should, in principle, allow the 3'-OH group to be blocked by a cleavable moiety that is small enough to be accepted by DNA polymerases. In this architecture, multiple cleavage steps might be required to remove both the tag (to make the system clean for the addition of the next tag) and the 3'-blocking group, to permit the next cycle of extension to occur [Mit03][Seo04].

U.S. Pat. No. 6,664,079 then struggled to find a small chemical group that might be accepted by polymerases, and could be removed under conditions that were not so harsh as to destroy the DNA being sequenced or the architecture supporting the sequences. U.S. Pat. No. 6,664,079 cited a literature report that 3'-O-methoxy-deoxynucleotides are good substrates for several polymerases [Axe78]. It noted, correctly, that the conditions for removing a 3'-O methyl group were too stringent to permit this blocking group from being removed under any conditions that were likely to leave the DNA being sequenced, or the primer that was being used, largely intact.

An ester group was also discussed as a way to cap the 3'-OH group of the nucleotide. U.S. Pat. No. 6,664,079 discarded this blocking group based on a report that esters are cleaved in the active site in DNA polymerase [Can95]. It should be noted that this report is questionable, and considers only a single polymerase. Therefore, in a modification not considered by Ju et al. a formyl group may be used in this architecture. The 3'-O formylated 2'-deoxynucleoside triphosphates are preparable as intermediates in the Ludwig-Eckstein triphosphate synthesis, if the 3'-O acetyl group that is traditionally used is replaced by a formyl group, and the final alkaline deprotection step is omitted.

U.S. Pat. No. 6,664,079 then cited a literature report that 3'-O-allyl-dATP is incorporated by Vent (exo-) DNA polymerase in the growing strand of DNA [Met94]. U.S. Pat. No. 6,664,079 noted that this group, and the methoxymethyl MOM group, having a similar size, might be used to cap the 3'-OH group in a sequencing-during-synthesis format. This patent noted that these groups can be cleaved chemically using transition metal reagents [Ire86][Kam99], or through acidic reagents (for the MOM group).

These suggestions therefore define the invention proposed in U.S. Pat. No. 6,664,079. Briefly, the essence of that invention is an architecture where the triphosphates of four nucleotide analogues, each labeled with a distinctive cleavable tag attached to the nucleobase, and each having the hydrogen of the 3'-OH group capped replaced by an allyl group or a MOM group, are used as the triphosphates in the sequencing by synthesis architecture, and the products are oligonucleotides prepared by polymerase incorporation that have this replacement.

This architecture, to date, has never been reduced to practice. This is again because of the polymerases. While the allyl group is small, to date, no polymerases have been shown to incorporate these to the extent and with the efficiency needed to effectively reduce this invention to practice. Therefore, U.S. Pat. No. 6,664,079 cannot be said to have enabled the sequencing-by-synthesis strategy. Further, more recent literature has described the use of Therminator variants to incorporate these MOM- and allyl-protected nucleoside triphosphates. Therminator has many disadvantages that make it difficult to apply in practice. Not the least of these is the affinity with which it binds to template-primer overhangs and single stranded DNA, an affinity that makes it difficult to wash in repetitive sequencing-during-synthesis architectures.

Recent patent applications have disclosed a smaller 3'-blocking group, one that has fewer than three heavy (that is, non-hydrogen) atoms. Their disclosures taught that such a blocking group is useful for an efficient sequencing-during-synthesis architecture, either with natural polymerases or with polymerases in which one of the amino acids in contact with the ribose ring is mutated. These might include the formyl unit, where the hydrogen atom of the 3'-OH group is replaced by a COH unit.

In the disclosed invention, the preferred replacement is $NH_2$ or NHR. There, the 3'-O-amino group is used as a removable protecting group for the sequencing-by-synthesis scheme. The 3'-O-amino group is chosen is as small a moiety that forms a stable 3'-O blocking group. The small size of the 3'-modification makes it most likely to be accepted by DNA polymerases during template-directed DNA polymerization [Hen04].

Further, contact by DNA polymerases with the 3'-end of the incoming triphosphate is frequently made with an amino acid with an aromatic side chain (Phe or Tyr) [Gar99]. The size of this can be reduced (to His), generating the possibility that if any particular natural polymerase does not work, then these can be mutated, followed by a round of in vitro directed evolution [Gha01], to generate polymerases that accept 3'-O-amino triphosphates with acceptable specifications.

The hydroxylamine functionality is stable in water, and displays several other advantages:

(a) 3'-O-Amino-2'-deoxynucleosides [DeC90][Kon85] [Bur94][Coo94] are directly synthesizable from the xylo-2'-deoxyribonucleosides via a Mitsunobu reaction with N-hydroxyphthalimide.

(b) The 3'-O-amino-2'-deoxynucleoside blocking group is small, even smaller than the speculative —OSH unit (which is considered in the instant invention) and the azido unit (which is incorporated by reverse transcriptases when they accept azidothymidine triphosphate, for example).

(c) The 3'-O-amino-2'-deoxynucleoside functionality has much of the hydrogen bonding potential of the 3'-OH group. While not wishing to be bound by theory, these derivatives may form a network of hydrogen bonds to the catalytic magnesium ion, as suggested by crystallography for the natural substrate, and therefore fitting into the active site of various polymerases.

(d) In some cases, a polymerase can be improved by replacing the Phe or Tyr (depending on the polymerase) [Eva00][Gar99] that blocks the 3'-position of the incoming triphosphate with a slightly smaller aromatic and/or hydrophobic group, His/Phe/Val.

(e) A large number of reagents are known that cleave the N—O linkage in hydroxylamines and O-alkoxyamines. These are discussed in greater detail below. Oxidative conditions are provided by bleach, nitrous acid at pH 6 under conditions where the nucleobases are not significantly modified, nitroso compounds, iodate, or potassium ferrate in 1 M NaCl, 50 mM potassium phosphate buffer, 25° C.; this generates the free —OH group and $N_2O$, which is trapped. Reducing agents include catalytic hydrogenation. The preferred approaches include addition-elimination cycles where the amino group of the alkoxyamine adds to an electrophile (such as maleimide or a naphthoquinone) and then ejects the alcohol as a leaving group.

(f) Once incorporated, the product 3'-O-amino-oligo-2'-deoxyribonucleosides themselves have value, through capture architectures that exploit the 3'-blocking group or, after its removal, as the starting point for cloning and further elongation processes.

With this 3'-O blocking group, other features of the architecture of the state-of-the-art sequencing-by-synthesis approach can be adopted. In particular, the linkers that hold the fluorescent labels to the nucleobases in the Ju architecture might be cleaved using the same reagent is used to remove the amino group from the terminal 3'-O-amino-2'-deoxynucleoside.

BRIEF DESCRIPTION OF THE DRAWINGS

FIG. 1. Amino acid sequence of wild-type DNA Polymerase from *Thermus aquaticus*. Underlined sites represent positions hosting amino acid replacements identified by the process disclosed here.

FIG. 2. An example multiple sequence alignment between the amino acid sequence of the wild-type DNA polymerase from *Thermus aquaticus* and sequences from homologs of Taq polymerase. This represents a partial list of Taq homologs. Taq sites are listed for positions 451-830 only since the replacements identified by the process disclosed here are located in this domain of the protein. DNA polymerase sequences homologous to *Thermus aquaticus* (THEAQ) are listed for *Homo sapiens* (HUMAN), *Saccharomyces cerevisiae* (YEAST), *Deinococcus radiodurans* (DEIRA), *Escherichia coli* (ECOLI), *Haemophilus influenzae* (HAEIN), *Bacillus stearothermophilus* (BACST), *Streptococcus pneumoniae* strain R6 (STRR6), *Mycobacterium tuberculosis* (MYCTU), *Bacillus phage* SPO1 (BPSP 1), *Mycobacterium phage* L5 (BPML5), Bacteriophage T7 (BPT7). Underlined sites in the *Thermus aquaticus* (THEAQ) sequence represent positions hosting amino acid replacements identified by the process disclosed here. Gaps are represented with a period.

DETAILED DESCRIPTION OF THE INVENTION

Engineering DNA Polymerases

The DNA polymerase from *Thermus aquaticus* (Taq) is commonly used for Sanger-based sequencing methods and it is known to release primer/template complexes. Unfortunately, wild-type Taq polymerase may not be able to incorporate T-$ONH_2$ well enough to support the sequencing-by-synthesis method outlined above, or other versions of it. Polymerases that have had amino acid replacement(s) (one or more) so that the variant polymerase (defined here to be different from the parent polymerase, which may be the same or different from a polymerase found in nature) that accept triphosphates modified to carry reversibly terminating units (on the sugars as well as elsewhere, such as on the nucleobases) will therefore have utility.

A process to construct useful variants, or the novel compositions that those variants are, must begin with a process that identifies sites in a polymerase protein sequence where the amino acid is changed. A "site" is, as defined here", specified by a number in a sequence of amino acids, where that number is defined by reference to a figure that lists the amino acids of the protein in that sequence. Disclosed elsewhere (e.g. U.S. Pat. No. 5,958,784) is a semi-rational approach, defined here as a "phylogenetic-based approach", which begins by the process of analyzing the patterns of change and conservation among a set of homologous proteins. This process comprises some or all of the following steps: constructing evolutionary trees from the multiple sequence alignment, inferring the sequences of ancestral proteins at nodes in the tree, applying phylogenetic tools to identify signals/sites associated with functional divergence, and examining these sites together with a model representing the three dimensional structure of the protein. This approach identifies a small number of sites where amino acid replacement might yield a useful protein, specifically, one that is not catalytically active or that does not fold properly. Thus, this process complements other directed evolution approached.

To apply this process to DNA polymerases that are members of evolutionary family A, the sequences of 719 polymerases from Family A were collected from the PFAM database (PF00476) [Bat04]. A phylogenetic tree representing the evolutionary relationship of these polymerases was obtained from the PFAM database (PF00476) [Bat04]. Metrics used to infer functional divergence were applied to the dataset. This computational phylogenetic-based approach confirmed what was already proposed in the literature: functional divergence of polymerase behaviors has occurred along branches of the phylogeny separating viral and non-viral polymerases [Hor95][Lea06][Sis06][Tab95]. Owing to the fact that viral polymerases are inherently more likely to accept modified nucleotides than non-viral polymerases, the phylogenetic-based approach implied that sites identified as being responsible for functional divergence between viral and non-viral polymerases would be sites that, in the non-viral polymerases, could have their amino acids replaced to generate new polymerase variants with useful properties.

Making reference to a model for the three dimensional crystal structure of polymerases, phylogenetic-based analysis identified sites both within and without the active-site cleft of the polymerase. Rationally, sites within the active site are more likely to alter substrate specificity [Hen05]. Amino acid replacements distributed across 35 of these sites were identified as having potential interest. According to the process of the invention, one of these sites may be changed, or more than one of these sites may be changed, to generate a useful polymerase. Further, these sites may be changed starting with a polymerase parent from any member of Family A (either as found naturally or as found from a laboratory that has already one or more amino acids different from a natural Family A polymerase.

Example 1

Useful, Novel Variants of Taq Polymerase

The Taq polymerase protein is widely used for sequencing DNA. Standard experimental approaches are used to perform site-directed mutagenesis to incorporate the amino acid replacements at sites listed in the Claims. For instance, mutagenic PCR is performed on a template Family A polymerase gene using the appropriate mutagenic primers to generate variants containing amino acid replacements. The PCR mixtures contain the following: 1× Mutagenic Taq Buffer (10 mM Tris-HCl, pH 8.3, 50 mM KCl, 15 mM $MgCl_2$), 0.1 ng/µL template DNA, 200 µM dNTPs, 300 nM P-4, 300 nM mutagenic primers, 5 U Taq polymerase (New England BioLabs, Beverly, Mass.), and $MgCl_2$. PCR reaction continues as follows: 5 min, 94° C.; (30 s, 94.0° C.; 20 s, 55.0° C.; 3 min, 72.0° C.)×15 cycles; 7 min, 72.0° C.; 4.0° C. Products can purified with the QIAquick PCR Purification Kit (Qiagen, Valencia, Calif.), eluted with Qiagen Buffer EB (50 µL), and quantitated at an absorbance of 260 nm using a Spectrophotometer.

This invention provides new sequences of proteins that are likely to accept nucleoside 3'-$ONH_2$ blocked triphosphates, dideoxynucleoside triphosphates and C-glycosides such as 2'-deoxypseudouridine-5'-triphosphate.

REFERENCES

[Axe78] Axelrod, V. D., Vartikyan, R. M., Aivazashvili, V. A., Beabealashvili, R. S. (1978) Specific termination of RNA polymerase synthesis as a method of RNA and DNA sequencing. *Nucleic Acids Res.* 5, 3549-3563

[Bat04] Bateman, A., Coin, L., Durbin, R., et al. (2004) The Pfam protein families database. *Nucleic Acids Res,* 32, D138-41.

[Bur94] Burgess, K., Gibbs, R. A., Metzker, M. L., Raghavachari, R. (1994) Synthesis of an oxyamide linked nucleotide dimer and incorporation into antisense oligonucleotide sequences. *J. Chem. Soc. Chem. Commun.* 8, 915-916

[Can95] Canard, B., Cardona, B., Sarfati, R. S. (1995) Catalytic editing properties of DNA polymerases. *Proc. Natl. Acad Sci. USA* 92, 10859-10863

[Che94] Cheeseman, P. C. (1994) Method For Sequencing Polynucleotides, U.S. Pat. No. 5,302,509, issued Apr. 12, 1994

[Coo94] Cook, P. D., Sanghvi, Y. S. (1994) Preparation of antisense heteroatomic oligonucleotide analogs. *PCT Int. Appl.* 90 pp

[DeC90] De Clercq, E., Inoue, I., Kondo, K. (1990) Preparation of 3-O-amino-2'-deoxyribonucleoside derivatives as antiviral agents for human retrovirus, particularly human immunodeficiency virus. *Eur. Pat. Appl.* 14 pp

[Eva00] Evans, S. J., Fogg, M. J., Mamone, A., Davis, M., Pearl, L. H., Connolly, B. A. (2000) Improving dideoxynucleotide-triphosphate utilisation by the hyper-thermophilic DNA polymerase from the archaeon *Pyrococcus furiosus. Nucl. Acids Res.* 28, 1059-1066

[Gar99] Gardner, F., Jack, W. E. (1999) Determinants of nucleotide sugar recognition in archaeon DNA polymerase. *Nucl. Acids Res.* 27, 2545-2553

[Gha01] Ghadessy, F. J., Ong, J. L., Holliger, P. (2001) Directed evolution of polymerase function by compartmentalized self-replication. *Proc. Natl. Acad. Sci. USA* 98:4552-4557.

[Hen04] Hendrickson, C., Devine, K., Benner, S. A. (2004) Probing the necessity of minor groove interactions with three DNA polymerase families using 3-deaza-2'-deoxyadenosine 5'-triphosphate. *Nucl. Acids Res.* 32, 2241-2250

[Hen05] Henry, A. A. & Romesberg, F. E. (2005) The evolution of DNA polymerases with novel activities. *Curr Opin Biotechnol,* 16, 370-7.

[Hor95] Horlacher, J., Hottiger, M., Podust, V. N., Hubscher, U. & Benner, S. A. (1995) Recognition by viral and cellular DNA polymerases of nucleosides bearing bases with nonstandard hydrogen bonding patterns. *Proc Natl Acad Sci USA,* 92, 6329-33.

[Hym88] Hyman, E. D. (1988) A new method of sequencing DNA. *Anal. Biochem.* 174, 423-436

[Ire86] Ireland, R. E., Varney, M. D. (1986) Approach to the total synthesis of chlorothricolide-synthesis of (+/−)-19.20-dihydro-24-O-methylchlorothricolide, methyl-ester, ethyl carbonate. *J Org. Chem.* 51, 635-648

[Ju95] Ju, J., Glazer, A. N., Mathies, P. A. (1996) Cassette labeling for facile construction of energy transfer fluorescent primers. *Nucleic Acids Res.* 24, 1144-1148

[Ju96] Ju, J., Ruan, C., Fuller, C. W., Glazer, A. N., Mathies, R. A. (1995) Energy transfer fluorescent dye-labeled primers for DNA sequencing and analysis. *Proc. Natl. Acad Sci. USA* 92, 4347-4351

[Kam99] Kamal, A., Laxman, E., Rao, N. V. (1999) A mild and rapid regeneration of alcohols from their allylic ethers by chlorotrimethylsilane/sodium iodide. *Tetrahedron Lett.* 40, 371-372.

[Lea06] Leal, N. A., Sukeda, M. & Benner, S. A. (2006) Dynamic assembly of primers on nucleic acid templates. *Nucleic Acids Res,* 34, 4702-10.

[Met94] Metzker, M. L., Raghavachari, R., Richards, S., Jacutin, S. E., Civitello, A., Burgess, K., Gibbs, R. A. (1994) Termination of DNA synthesis by novel 3'-modified-deoxyribonucleoside 5'-triphosphates. *Nucleic Acids Res.* 22, 4259-4267

[Mit03] Mitra, R. D., Shendure, J., Olejnik, J., Olejnik, E. K., Church, G. M. (2003) Fluorescent in situ sequencing on polymerase colonies. *Anal. Biochem.* 320, 55-65.

[Ron98] Ronaghi, M., Uhlen, M., Nyren, P. (1998) A sequencing method based on real-time pyrophosphate. *Science* 281, 364-365

[Ros00] Roses, A. (2000) Pharmacogenetics and the practice of medicine. *Nature* 405, 857-865

[Sal98] Salas-Solano, O., Carrilho, E., Kotler, L., Miller, A. W., Goetzinger, W., Sosic, Z., Karger, B. L. (1998) Routine DNA sequencing of 1000 bases in less than one hour by capillary electrophoresis with replaceable linear polyacrylamide solutions. *Anal. Chem.* 70, 3996-4003

[Seo04] Seo, T. S., Bai, X., Ruparel, H., Li, Z., Turro, N. J., Ju, J. (2004). Photocleavable fluorescent nucleotides for DNA sequencing on a chip constructed by site-specific coupling chemistry. *Proc. Natl. Acad. Sci. USA* 101, 5488-5493

[Sis06] Sismour, A. M., Lutz, S., Park, J. H., et al. (2004) PCR amplification of DNA containing non-standard base pairs by variants of reverse transcriptase from Human Immunodeficiency Virus-1. *Nucleic Acids Research,* 32, 728-735.

[Smi86] Smith, L. M., Sanders, J. Z., Kaiser, R. J., Hughes, P., Dodd, C., Connell, C. R., Heiner, C., Kent, S. B. H., Hood, L. E. (1986) Fluorescence detection in automated DNA sequencing analysis. *Nature* 321, 674-679

[Tab87] Tabor, S., Richardson, C. C. (1987) DNA sequence analysis with a modified bacteriophage T7 DNA polymerase. *Proc. Natl. Acad. Sci. USA* 84, 4767-4771

[Tab95] Tabor, S., Richardson, C. C. (1995) A single residue in DNA polymerases of the *Escherichia coli* DNA polymerase I family is critical for distinguishing between deoxy- and dideoxyribonucleotides. *Proc. Natl. Acad. Sci. USA* 92, 6339-6343

[Wel99] Welch, M. B., Burgess, K. (1999) Synthesis of fluorescent, photolabile 3'-O-protected nucleoside triphosphates for the base addition sequencing scheme. *Nucleosides Nucleotides* 18,197-201

---

What is claimed is:

1. A DNA polymerase from *Thermus aquaticus* wherein the amino acid at position 616, as defined by SEQ ID NO:1, is replaced by an amino acid selected from the group consisting of Ala, Arg, Cys, Glu, Gln, Gly, His, Ile, Lys, Met, Phe, Ser, Thr, Trp, Tyr, Val and Asp.

* * * * *

SEQUENCE LISTING

```
<160> NUMBER OF SEQ ID NOS: 12

<210> SEQ ID NO 1
<211> LENGTH: 832
<212> TYPE: PRT
<213> ORGANISM: Thermus aquaticus

<400> SEQUENCE: 1

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205
```

```
Glu Glu Trp Gly Ser Leu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Ala Pro Trp Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Val Arg Leu Leu Trp Leu Tyr Arg Glu
            420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
    610                 615                 620
```

```
Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
            645                 650                 655

Leu Met Arg Arg Ala Ala Lys Thr Ile Asn Phe Gly Val Leu Tyr Gly
        660                 665                 670

Met Ser Ala His Arg Leu Ser Gln Glu Leu Ala Ile Pro Tyr Glu Glu
    675                 680                 685

Ala Gln Ala Phe Ile Glu Arg Tyr Phe Gln Ser Phe Pro Lys Val Arg
690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Tyr Val Pro Asp Leu Glu Ala Arg
                725                 730                 735

Val Lys Ser Val Arg Glu Ala Ala Glu Arg Met Ala Phe Asn Met Pro
                740                 745                 750

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 2
<211> LENGTH: 928
<212> TYPE: PRT
<213> ORGANISM: Escherichia coli

<400> SEQUENCE: 2

Met Val Gln Ile Pro Gln Asn Pro Leu Ile Leu Val Asp Gly Ser Ser
1               5                   10                  15

Tyr Leu Tyr Arg Ala Tyr His Ala Phe Pro Pro Leu Thr Asn Ser Ala
                20                  25                  30

Gly Glu Pro Thr Gly Ala Met Tyr Gly Val Leu Asn Met Leu Arg Ser
            35                  40                  45

Leu Ile Met Gln Tyr Lys Pro Thr His Ala Ala Val Val Phe Asp Ala
50                  55                  60

Lys Gly Lys Thr Phe Arg Asp Glu Leu Phe Glu His Tyr Lys Ser His
65                  70                  75                  80

Arg Pro Pro Met Pro Asp Asp Leu Arg Ala Gln Ile Glu Pro Leu His
                85                  90                  95

Ala Met Val Lys Ala Met Gly Leu Pro Leu Leu Ala Val Ser Gly Val
            100                 105                 110

Glu Ala Asp Asp Val Ile Gly Thr Leu Ala Arg Glu Ala Glu Lys Ala
        115                 120                 125

Gly Arg Pro Val Leu Ile Ser Thr Gly Asp Lys Asp Met Ala Gln Leu
    130                 135                 140

Val Thr Pro Asn Ile Thr Leu Ile Asn Thr Met Thr Asn Thr Ile Leu
145                 150                 155                 160

Gly Pro Glu Glu Val Val Asn Lys Tyr Gly Val Pro Pro Glu Leu Ile
                165                 170                 175
```

```
Ile Asp Phe Leu Ala Leu Met Gly Asp Ser Ser Asp Asn Ile Pro Gly
            180                 185                 190

Val Pro Gly Val Gly Glu Lys Thr Ala Gln Ala Leu Leu Gln Gly Leu
            195                 200                 205

Gly Gly Leu Asp Thr Leu Tyr Ala Glu Pro Glu Lys Ile Ala Gly Leu
            210                 215                 220

Ser Phe Arg Gly Ala Lys Thr Met Ala Ala Lys Leu Glu Gln Asn Lys
225                 230                 235                 240

Glu Val Ala Tyr Leu Ser Tyr Gln Leu Ala Thr Ile Lys Thr Asp Val
                245                 250                 255

Glu Leu Glu Leu Thr Cys Glu Gln Leu Glu Val Gln Gln Pro Ala Ala
            260                 265                 270

Glu Glu Leu Leu Gly Leu Phe Lys Lys Tyr Glu Phe Lys Arg Trp Thr
            275                 280                 285

Ala Asp Val Glu Ala Gly Lys Trp Leu Gln Ala Lys Gly Ala Lys Pro
            290                 295                 300

Ala Ala Lys Pro Gln Glu Thr Ser Val Ala Asp Glu Ala Pro Glu Val
305                 310                 315                 320

Thr Ala Thr Val Ile Ser Tyr Asp Asn Tyr Val Thr Ile Leu Asp Glu
                325                 330                 335

Glu Thr Leu Lys Ala Trp Ile Ala Lys Leu Glu Lys Ala Pro Val Phe
            340                 345                 350

Ala Phe Asp Thr Glu Thr Asp Ser Leu Asp Asn Ile Ser Ala Asn Leu
            355                 360                 365

Val Gly Leu Ser Phe Ala Ile Glu Pro Gly Val Ala Ala Tyr Ile Pro
            370                 375                 380

Val Ala His Asp Tyr Leu Asp Ala Pro Asp Gln Ile Ser Arg Glu Arg
385                 390                 395                 400

Ala Leu Glu Leu Leu Lys Pro Leu Leu Glu Asp Glu Lys Ala Leu Lys
                405                 410                 415

Val Gly Gln Asn Leu Lys Tyr Asp Arg Gly Ile Leu Ala Asn Tyr Gly
            420                 425                 430

Ile Glu Leu Arg Gly Ile Ala Phe Asp Thr Met Leu Glu Ser Tyr Ile
            435                 440                 445

Leu Asn Ser Val Ala Gly Arg His Asp Met Asp Ser Leu Ala Glu Arg
            450                 455                 460

Trp Leu Lys His Lys Thr Ile Thr Phe Glu Glu Ile Ala Gly Lys Gly
465                 470                 475                 480

Lys Asn Gln Leu Thr Phe Asn Gln Ile Ala Leu Glu Glu Ala Gly Arg
                485                 490                 495

Tyr Ala Ala Glu Asp Ala Asp Val Thr Leu Gln Leu His Leu Lys Met
            500                 505                 510

Trp Pro Asp Leu Gln Lys His Lys Gly Pro Leu Asn Val Phe Glu Asn
            515                 520                 525

Ile Glu Met Pro Leu Val Pro Val Leu Ser Arg Ile Glu Arg Asn Gly
            530                 535                 540

Val Lys Ile Asp Pro Lys Val Leu His Asn His Ser Glu Glu Leu Thr
545                 550                 555                 560

Leu Arg Leu Ala Glu Leu Glu Lys Lys Ala His Glu Ile Ala Gly Glu
                565                 570                 575

Glu Phe Asn Leu Ser Ser Thr Lys Gln Leu Gln Thr Ile Leu Phe Glu
            580                 585                 590
```

```
Lys Gln Gly Ile Lys Pro Leu Lys Thr Pro Gly Ala Pro Ser
            595             600             605

Thr Ser Glu Glu Val Leu Glu Leu Ala Leu Asp Tyr Pro Leu Pro
610             615                 620

Lys Val Ile Leu Glu Tyr Arg Gly Leu Ala Lys Leu Lys Ser Thr Tyr
625                 630                 635                 640

Thr Asp Lys Leu Pro Leu Met Ile Asn Pro Lys Thr Gly Arg Val His
                645                 650                 655

Thr Ser Tyr His Gln Ala Val Thr Ala Thr Gly Arg Leu Ser Ser Thr
                660                 665                 670

Asp Pro Asn Leu Gln Asn Ile Pro Val Arg Asn Glu Glu Gly Arg Arg
            675                 680                 685

Ile Arg Gln Ala Phe Ile Ala Pro Glu Asp Tyr Val Ile Val Ser Ala
690                 695                 700

Asp Tyr Ser Gln Ile Glu Leu Arg Ile Met Ala His Leu Ser Arg Asp
705                 710                 715                 720

Lys Gly Leu Leu Thr Ala Phe Ala Glu Gly Lys Asp Ile His Arg Ala
                725                 730                 735

Thr Ala Ala Glu Val Phe Gly Leu Pro Leu Glu Thr Val Thr Ser Glu
            740                 745                 750

Gln Arg Arg Ser Ala Lys Ala Ile Asn Phe Gly Leu Ile Tyr Gly Met
            755                 760                 765

Ser Ala Phe Gly Leu Ala Arg Gln Leu Asn Ile Pro Arg Lys Glu Ala
            770                 775                 780

Gln Lys Tyr Met Asp Leu Tyr Phe Glu Arg Tyr Pro Gly Val Leu Glu
785                 790                 795                 800

Tyr Met Glu Arg Thr Arg Ala Gln Ala Lys Glu Gln Gly Tyr Val Glu
                805                 810                 815

Thr Leu Asp Gly Arg Arg Leu Tyr Leu Pro Asp Ile Lys Ser Ser Asn
            820                 825                 830

Gly Ala Arg Arg Ala Ala Ala Glu Arg Ala Ala Ile Asn Ala Pro Met
                835                 840                 845

Gln Gly Thr Ala Ala Asp Ile Ile Lys Arg Ala Met Ile Ala Val Asp
850                 855                 860

Ala Trp Leu Gln Ala Glu Gln Pro Arg Val Arg Met Ile Met Gln Val
865                 870                 875                 880

His Asp Glu Leu Val Phe Glu Val His Lys Asp Val Asp Ala Val
                885                 890                 895

Ala Lys Gln Ile His Gln Leu Met Glu Asn Cys Thr Arg Leu Asp Val
            900                 905                 910

Pro Leu Leu Val Glu Val Gly Ser Gly Glu Asn Trp Asp Gln Ala His
            915                 920                 925

<210> SEQ ID NO 3
<211> LENGTH: 876
<212> TYPE: PRT
<213> ORGANISM: Bacillus stearothermophilus

<400> SEQUENCE: 3

Met Lys Asn Lys Leu Val Leu Ile Asp Gly Asn Ser Val Ala Tyr Arg
1               5                   10                  15

Ala Phe Phe Ala Leu Pro Leu Leu His Asn Asp Lys Gly Ile His Thr
                20                  25                  30

Asn Ala Val Tyr Gly Phe Thr Met Met Leu Asn Lys Ile Leu Ala Glu
            35                  40                  45
```

-continued

```
Glu Gln Pro Thr His Ile Leu Val Ala Phe Asp Ala Gly Lys Thr Thr
     50                  55                  60
Phe Arg His Glu Thr Phe Gln Asp Tyr Lys Gly Arg Gln Gln Thr
 65                  70                  75                  80
Pro Pro Glu Leu Ser Glu Gln Phe Pro Leu Leu Arg Glu Leu Leu Lys
                     85                  90                  95
Ala Tyr Arg Ile Pro Ala Tyr Glu Leu Asp His Tyr Glu Ala Asp Asp
                100                 105                 110
Ile Ile Gly Thr Met Ala Ala Arg Ala Glu Arg Glu Gly Phe Ala Val
             115                 120                 125
Lys Val Ile Ser Gly Asp Arg Asp Leu Thr Gln Leu Ala Ser Pro Gln
130                 135                 140
Val Thr Val Glu Ile Thr Lys Lys Gly Ile Thr Asp Ile Glu Ser Tyr
145                 150                 155                 160
Thr Pro Glu Thr Val Val Glu Lys Tyr Gly Leu Thr Pro Glu Gln Ile
                165                 170                 175
Val Asp Leu Lys Gly Leu Met Gly Asp Lys Ser Asp Asn Ile Pro Gly
             180                 185                 190
Val Pro Gly Ile Gly Glu Lys Thr Ala Val Lys Leu Leu Lys Gln Phe
         195                 200                 205
Gly Thr Val Glu Asn Val Leu Ala Ser Ile Asp Glu Ile Lys Gly Glu
     210                 215                 220
Lys Leu Lys Glu Asn Leu Arg Gln Tyr Arg Asp Leu Ala Leu Leu Ser
225                 230                 235                 240
Lys Gln Leu Ala Ala Ile Cys Arg Asp Ala Pro Val Glu Leu Thr Leu
                245                 250                 255
Asp Asp Ile Val Tyr Lys Gly Asp Arg Glu Lys Val Val Ala Leu
             260                 265                 270
Phe Gln Glu Leu Gly Phe Gln Ser Phe Leu Asp Lys Met Ala Val Gln
         275                 280                 285
Thr Asp Glu Gly Glu Lys Pro Leu Ala Gly Met Asp Phe Ala Ile Ala
     290                 295                 300
Asp Ser Val Thr Asp Glu Met Leu Ala Asp Lys Ala Ala Leu Val Val
305                 310                 315                 320
Glu Val Val Gly Asp Asn Tyr His His Ala Pro Ile Val Gly Ile Ala
                325                 330                 335
Leu Ala Asn Glu Arg Gly Arg Phe Phe Leu Arg Pro Glu Thr Ala Leu
             340                 345                 350
Ala Asp Pro Lys Phe Leu Ala Trp Leu Gly Asp Glu Thr Lys Lys Lys
         355                 360                 365
Thr Met Phe Asp Ser Lys Arg Ala Ala Val Ala Leu Lys Trp Lys Gly
     370                 375                 380
Ile Glu Leu Arg Gly Val Val Phe Asp Leu Leu Leu Ala Ala Tyr Leu
385                 390                 395                 400
Leu Asp Pro Ala Gln Ala Ala Gly Asp Val Ala Val Ala Lys Met
                405                 410                 415
His Gln Tyr Glu Ala Val Arg Ser Asp Glu Ala Val Tyr Gly Lys Gly
             420                 425                 430
Ala Lys Arg Thr Val Pro Asp Glu Pro Thr Leu Ala Glu His Leu Val
         435                 440                 445
Arg Lys Ala Ala Ala Ile Trp Ala Leu Glu Glu Pro Leu Met Asp Glu
     450                 455                 460
```

-continued

```
Leu Arg Arg Asn Glu Gln Asp Arg Leu Leu Thr Glu Leu Glu Gln Pro
465                 470                 475                 480

Leu Ala Gly Ile Leu Ala Asn Met Glu Phe Thr Gly Val Lys Val Asp
            485                 490                 495

Thr Lys Arg Leu Glu Gln Met Gly Ala Glu Leu Thr Glu Gln Leu Gln
        500                 505                 510

Ala Val Glu Arg Arg Ile Tyr Glu Leu Ala Gly Gln Glu Phe Asn Ile
    515                 520                 525

Asn Ser Pro Lys Gln Leu Gly Thr Val Leu Phe Asp Lys Leu Gln Leu
530                 535                 540

Pro Val Leu Lys Lys Thr Lys Thr Gly Tyr Ser Thr Ser Ala Asp Val
545                 550                 555                 560

Leu Glu Lys Leu Ala Pro His His Glu Ile Val Glu His Ile Leu His
            565                 570                 575

Tyr Arg Gln Leu Gly Lys Leu Gln Ser Thr Tyr Ile Glu Gly Leu Leu
        580                 585                 590

Lys Val Val His Pro Val Thr Gly Lys Val His Thr Met Phe Asn Gln
    595                 600                 605

Ala Leu Thr Gln Thr Gly Arg Leu Ser Ser Val Glu Pro Asn Leu Gln
    610                 615                 620

Asn Ile Pro Ile Arg Leu Glu Glu Gly Arg Lys Ile Arg Gln Ala Phe
625                 630                 635                 640

Val Pro Ser Glu Pro Asp Trp Leu Ile Phe Ala Ala Asp Tyr Ser Gln
            645                 650                 655

Ile Glu Leu Arg Val Leu Ala His Ile Ala Glu Asp Asp Asn Leu Ile
        660                 665                 670

Glu Ala Phe Arg Arg Gly Leu Asp Ile His Thr Lys Thr Ala Met Asp
    675                 680                 685

Ile Phe His Val Ser Glu Glu Asp Val Thr Ala Asn Met Arg Arg Gln
    690                 695                 700

Ala Lys Ala Val Asn Phe Gly Ile Val Tyr Gly Ile Ser Asp Tyr Gly
705                 710                 715                 720

Leu Ala Gln Asn Leu Asn Ile Thr Arg Lys Glu Ala Ala Glu Phe Ile
            725                 730                 735

Glu Arg Tyr Phe Ala Ser Phe Pro Gly Val Lys Gln Tyr Met Asp Asn
        740                 745                 750

Ile Val Gln Glu Ala Lys Gln Lys Gly Tyr Val Thr Thr Leu Leu His
    755                 760                 765

Arg Arg Arg Tyr Leu Pro Asp Ile Thr Ser Arg Asn Phe Asn Val Arg
770                 775                 780

Ser Phe Ala Glu Arg Thr Ala Met Asn Thr Pro Ile Gln Gly Ser Ala
785                 790                 795                 800

Ala Asp Ile Ile Lys Lys Ala Met Ile Asp Leu Ser Val Arg Leu Arg
            805                 810                 815

Glu Glu Arg Leu Gln Ala Arg Leu Leu Leu Gln Val His Asp Glu Leu
        820                 825                 830

Ile Leu Glu Ala Pro Lys Glu Glu Ile Glu Arg Leu Cys Arg Leu Val
    835                 840                 845

Pro Glu Val Met Glu Gln Ala Val Thr Leu Arg Val Pro Leu Lys Val
    850                 855                 860

Asp Tyr His Tyr Gly Pro Thr Trp Tyr Asp Ala Lys
865                 870                 875
```

```
<210> SEQ ID NO 4
<211> LENGTH: 956
<212> TYPE: PRT
<213> ORGANISM: Deinococcus radiodurans

<400> SEQUENCE: 4

Met Val Phe Cys Gly Asp Gly Gly Leu Ser Cys Glu Ser Ile Asp Phe
1               5                   10                  15

Ala Leu Cys Cys Leu Arg Gly Arg Ser Gly Asn Tyr Val Gln Ser Arg
            20                  25                  30

Ile Leu Pro Met Ala Asp Ala Ser Pro Asp Pro Ser Lys Pro Asp Thr
        35                  40                  45

Leu Val Leu Ile Asp Gly His Ala Leu Ala Phe Arg Ser Tyr Phe Ala
50                  55                  60

Leu Pro Pro Leu Asn Asn Ser Lys Gly Glu Met Thr His Ala Ile Val
65                  70                  75                  80

Gly Phe Met Lys Leu Leu Arg Leu Ala Arg Gln Lys Ser Asn Gln
            85                  90                  95

Val Ile Val Val Phe Asp Pro Pro Val Lys Thr Phe Arg His Glu Gln
            100                 105                 110

Tyr Glu Gly Tyr Lys Ser Gly Arg Ala Gln Thr Pro Glu Asp Leu Pro
            115                 120                 125

Gly Gln Ile Asn Arg Ile Arg Ala Leu Val Asp Ala Leu Gly Phe Pro
        130                 135                 140

Arg Leu Glu Glu Pro Gly Tyr Glu Ala Asp Asp Val Ile Ala Ser Leu
145                 150                 155                 160

Thr Arg Met Ala Glu Gly Lys Gly Tyr Glu Val Arg Ile Val Thr Ser
            165                 170                 175

Asp Arg Asp Ala Tyr Gln Leu Leu Asp Glu His Val Lys Val Ile Ala
            180                 185                 190

Asn Asp Phe Ser Leu Ile Gly Pro Ala Gln Val Glu Glu Lys Tyr Gly
            195                 200                 205

Val Thr Val Arg Gln Trp Val Asp Tyr Arg Ala Leu Thr Gly Asp Ala
        210                 215                 220

Ser Asp Asn Ile Pro Gly Ala Lys Gly Ile Gly Pro Lys Thr Ala Ala
225                 230                 235                 240

Lys Leu Leu Gln Glu Tyr Gly Thr Leu Glu Lys Val Tyr Glu Ala Ala
            245                 250                 255

His Ala Gly Thr Leu Lys Pro Asp Gly Thr Arg Lys Lys Leu Leu Asp
            260                 265                 270

Ser Glu Glu Asn Val Lys Phe Ser His Asp Leu Ser Cys Met Val Thr
            275                 280                 285

Asp Leu Pro Leu Asp Ile Glu Phe Gly Val Arg Arg Leu Pro Asp Asn
        290                 295                 300

Pro Leu Val Thr Glu Asp Leu Leu Thr Glu Leu Glu Leu His Ser Leu
305                 310                 315                 320

Arg Pro Met Ile Leu Gly Leu Asn Gly Pro Glu Gln Asp Gly His Ala
            325                 330                 335

Pro Asp Asp Leu Leu Glu Arg Glu His Ala Gln Thr Pro Glu Glu Asp
            340                 345                 350

Glu Ala Ala Ala Leu Pro Ala Phe Ser Ala Pro Glu Leu Ala Glu Trp
            355                 360                 365

Gln Thr Pro Ala Glu Gly Ala Val Trp Gly Tyr Val Leu Ser Arg Glu
        370                 375                 380
```

```
Asp Asp Leu Thr Ala Ala Leu Leu Ala Ala Ala Thr Phe Glu Asp Gly
385                 390                 395                 400

Val Ala Arg Pro Ala Pro Val Ser Glu Pro Asp Glu Trp Ala Gln Ala
            405                 410                 415

Glu Ala Pro Glu Asn Leu Phe Gly Leu Leu Pro Ser Asp Lys Pro
        420                 425                 430

Leu Thr Lys Lys Glu Gln Lys Ala Leu Glu Lys Ala Gln Lys Asp Ala
        435                 440                 445

Glu Lys Ala Arg Ala Lys Leu Arg Glu Gln Phe Pro Ala Thr Val Asp
    450                 455                 460

Glu Ala Glu Phe Val Gly Gln Arg Thr Val Thr Ala Ala Ala Lys
465                 470                 475                 480

Ala Leu Ala Ala His Leu Ser Val Arg Gly Thr Val Val Glu Pro Gly
                485                 490                 495

Asp Asp Pro Leu Leu Tyr Ala Tyr Leu Leu Asp Pro Ala Asn Thr Asn
            500                 505                 510

Met Pro Val Val Ala Lys Arg Tyr Leu Asp Arg Glu Trp Pro Ala Asp
        515                 520                 525

Ala Pro Thr Arg Ala Ala Ile Thr Gly His Leu Leu Arg Glu Leu Pro
        530                 535                 540

Pro Leu Leu Asp Asp Ala Arg Arg Lys Met Tyr Asp Glu Met Glu Lys
545                 550                 555                 560

Pro Leu Ser Gly Val Leu Gly Arg Met Glu Val Arg Gly Val Gln Val
                565                 570                 575

Asp Ser Asp Phe Leu Gln Thr Leu Ser Ile Gln Ala Gly Val Arg Leu
            580                 585                 590

Ala Asp Leu Glu Ser Gln Ile His Glu Tyr Ala Gly Glu Glu Phe His
            595                 600                 605

Ile Arg Ser Pro Lys Gln Leu Glu Thr Val Leu Tyr Asp Lys Leu Glu
            610                 615                 620

Leu Ala Ser Ser Lys Lys Thr Lys Leu Thr Gly Gln Arg Ser Thr Ala
625                 630                 635                 640

Val Ser Ala Leu Glu Pro Leu Arg Asp Ala His Pro Ile Ile Pro Leu
                645                 650                 655

Val Leu Glu Phe Arg Glu Leu Asp Lys Leu Arg Gly Thr Tyr Leu Asp
            660                 665                 670

Pro Ile Pro Asn Leu Val Asn Pro His Thr Gly Arg Leu His Thr Thr
        675                 680                 685

Phe Ala Gln Thr Ala Val Ala Thr Gly Arg Leu Ser Ser Leu Asn Pro
        690                 695                 700

Asn Leu Gln Asn Ile Pro Ile Arg Ser Glu Leu Gly Arg Glu Ile Arg
705                 710                 715                 720

Lys Gly Phe Ile Ala Glu Asp Gly Phe Thr Leu Ile Ala Ala Asp Tyr
            725                 730                 735

Ser Gln Ile Glu Leu Arg Leu Leu Ala His Ile Ala Asp Asp Pro Leu
            740                 745                 750

Met Gln Gln Ala Phe Val Glu Gly Ala Asp Ile His Arg Arg Thr Ala
        755                 760                 765

Ala Gln Val Leu Gly Leu Asp Glu Ala Thr Val Asp Ala Asn Gln Arg
        770                 775                 780

Arg Ala Ala Lys Thr Val Asn Phe Gly Val Leu Tyr Gly Met Ser Ala
785                 790                 795                 800
```

```
His Arg Leu Ser Asn Asp Leu Gly Ile Pro Tyr Ala Glu Ala Ala Thr
                805                 810                 815

Phe Ile Glu Ile Tyr Phe Ala Thr Tyr Pro Gly Ile Arg Arg Tyr Ile
            820                 825                 830

Asn His Thr Leu Asp Phe Gly Arg Thr His Gly Tyr Val Glu Thr Leu
            835                 840                 845

Tyr Gly Arg Arg Arg Tyr Val Pro Gly Leu Ser Ser Arg Asn Arg Val
        850                 855                 860

Gln Arg Glu Ala Glu Glu Arg Leu Ala Tyr Asn Met Pro Ile Gln Gly
865                 870                 875                 880

Thr Ala Ala Asp Ile Met Lys Leu Ala Met Val Gln Leu Asp Pro Gln
                885                 890                 895

Leu Asp Ala Ile Gly Ala Arg Met Leu Leu Gln Val His Asp Glu Leu
            900                 905                 910

Leu Ile Glu Ala Pro Leu Asp Lys Ala Glu Gln Val Ala Ala Leu Thr
        915                 920                 925

Lys Lys Val Met Glu Asn Val Val Gln Leu Lys Val Pro Leu Ala Val
930                 935                 940

Glu Val Gly Thr Gly Pro Asn Trp Phe Asp Thr Lys
945                 950                 955

<210> SEQ ID NO 5
<211> LENGTH: 930
<212> TYPE: PRT
<213> ORGANISM: Haemophilus influenzae

<400> SEQUENCE: 5

Met Ala Gln Ile Ala Thr Asn Pro Leu Val Leu Val Asp Gly Ser Ser
1               5                   10                  15

Tyr Leu Tyr Arg Ala Phe His Ala Phe Pro Ser Leu Thr Asn Ala Ala
            20                  25                  30

Gly Glu Pro Thr Ser Ala Met Tyr Gly Val Leu Asn Met Leu Lys Ser
        35                  40                  45

Leu Ile Ser Gln Val Gln Pro Thr His Ile Ala Val Val Phe Asp Ala
    50                  55                  60

Lys Gly Lys Thr Phe Arg Asp Glu Met Phe Glu Gln Tyr Lys Ser His
65              70                  75                  80

Arg Pro Pro Met Pro Asp Asp Leu Arg Lys Gln Ile Gln Pro Leu His
                85                  90                  95

Asp Met Ile Arg Ala Leu Gly Ile Pro Leu Leu Val Val Glu Gly Ile
            100                 105                 110

Glu Ala Asp Asp Val Ile Gly Thr Leu Ala Leu Gln Ala Ser Ser Leu
        115                 120                 125

Gly Lys Lys Val Leu Ile Ser Thr Gly Asp Lys Asp Met Ala Gln Leu
    130                 135                 140

Val Asp Asp Asn Ile Met Leu Ile Asn Thr Met Asn Asn Ser Leu Leu
145                 150                 155                 160

Asp Arg Lys Gly Val Ile Glu Lys Tyr Gly Ile Pro Pro Glu Leu Ile
                165                 170                 175

Ile Asp Tyr Leu Ala Leu Met Gly Asp Ser Ala Asp Asn Ile Pro Gly
            180                 185                 190

Val Ala Gly Val Gly Glu Lys Thr Ala Leu Gly Leu Leu Gln Gly Ile
        195                 200                 205

Gly Ser Met Ala Glu Ile Tyr Ala Asn Leu Glu Lys Val Ala Glu Leu
```

```
            210                 215                 220
Pro Ile Arg Gly Ala Lys Lys Leu Gly Glu Lys Leu Ala Glu Lys
225                 230                 235                 240

Asn Asn Ala Asp Leu Ser Tyr Thr Leu Ala Thr Ile Lys Thr Asp Val
                    245                 250                 255

Glu Leu Asn Val Thr Thr Asp Gln Leu Leu Gly Glu Ser Gln Lys
                260                 265                 270

Asp Gln Leu Ile Glu Tyr Phe Ala Arg Tyr Glu Phe Lys Arg Trp Leu
                275                 280                 285

Asn Glu Val Met Asn Gly Ala Asp Ser Ile Thr Gln Thr Thr Glu Gln
290                 295                 300

Pro Val Lys Met Asn Gln Tyr Lys Ala Thr Ser Gln Asp Gln Ser Ala
305                 310                 315                 320

Val Glu Asn Thr Pro Lys Ile Gln Ile Asp Arg Thr Lys Tyr Glu Thr
                    325                 330                 335

Leu Leu Thr Gln Ala Asp Leu Thr Arg Trp Ile Glu Lys Leu Asn Ala
                340                 345                 350

Ala Lys Leu Ile Ala Val Asp Thr Glu Thr Asp Ser Leu Asp Tyr Met
                355                 360                 365

Ser Ala Asn Leu Val Gly Ile Ser Phe Ala Leu Glu Asn Gly Glu Ala
370                 375                 380

Ala Tyr Leu Pro Leu Gln Leu Asp Tyr Leu Asp Ala Pro Lys Thr Leu
385                 390                 395                 400

Glu Lys Ser Thr Ala Leu Ala Ala Ile Lys Pro Ile Leu Glu Asn Pro
                405                 410                 415

Asn Ile His Lys Ile Gly Gln Asn Ile Lys Phe Asp Glu Ser Ile Phe
                420                 425                 430

Ala Arg His Gly Ile Glu Leu Gln Gly Val Glu Phe Asp Thr Met Leu
                435                 440                 445

Leu Ser Tyr Thr Leu Asn Ser Thr Gly Arg His Asn Met Asp Asp Leu
                450                 455                 460

Ala Lys Arg Tyr Leu Gly His Glu Thr Ile Ala Phe Glu Ser Leu Ala
465                 470                 475                 480

Gly Lys Gly Lys Ser Gln Leu Thr Phe Asn Gln Ile Pro Leu Glu Gln
                    485                 490                 495

Ala Thr Glu Tyr Ala Ala Glu Asp Ala Asp Val Thr Met Lys Leu Gln
                500                 505                 510

Gln Ala Leu Trp Leu Lys Leu Gln Glu Glu Pro Thr Leu Val Glu Leu
                515                 520                 525

Tyr Lys Thr Met Glu Leu Pro Leu Leu His Val Leu Ser Arg Met Glu
                530                 535                 540

Arg Thr Gly Val Leu Ile Asp Ser Asp Ala Leu Phe Met Gln Ser Asn
545                 550                 555                 560

Glu Ile Ala Ser Arg Leu Thr Ala Leu Glu Lys Gln Ala Tyr Ala Leu
                565                 570                 575

Ala Gly Gln Pro Phe Asn Leu Ala Ser Thr Lys Gln Leu Gln Glu Ile
                580                 585                 590

Leu Phe Asp Lys Leu Glu Leu Pro Val Leu Gln Lys Thr Pro Lys Gly
                595                 600                 605

Ala Pro Ser Thr Asn Glu Glu Val Leu Glu Glu Leu Ser Tyr Ser His
                610                 615                 620

Glu Leu Pro Lys Ile Leu Val Lys His Arg Gly Leu Ser Lys Leu Lys
625                 630                 635                 640
```

Ser Thr Tyr Thr Asp Lys Leu Pro Gln Met Val Asn Ser Gln Thr Gly
            645                 650                 655

Arg Val His Thr Ser Tyr His Gln Ala Val Thr Ala Thr Gly Arg Leu
            660                 665                 670

Ser Ser Ser Asp Pro Asn Leu Gln Asn Ile Pro Ile Arg Asn Glu Glu
            675                 680                 685

Gly Arg His Ile Arg Gln Ala Phe Ile Ala Arg Glu Gly Tyr Ser Ile
            690                 695                 700

Val Ala Ala Asp Tyr Ser Gln Ile Glu Leu Arg Ile Met Ala His Leu
705                 710                 715                 720

Ser Gly Asp Gln Gly Leu Ile Asn Ala Phe Ser Gln Gly Lys Asp Ile
            725                 730                 735

His Arg Ser Thr Ala Ala Glu Ile Phe Gly Val Ser Leu Asp Glu Val
            740                 745                 750

Thr Ser Glu Gln Arg Arg Asn Ala Lys Ala Ile Asn Phe Gly Leu Ile
            755                 760                 765

Tyr Gly Met Ser Ala Phe Gly Leu Ser Arg Gln Leu Gly Ile Ser Arg
            770                 775                 780

Ala Asp Ala Gln Lys Tyr Met Asp Leu Tyr Phe Gln Arg Tyr Pro Ser
785                 790                 795                 800

Val Gln Gln Phe Met Thr Asp Ile Arg Glu Lys Ala Lys Ala Gln Gly
            805                 810                 815

Tyr Val Glu Thr Leu Phe Gly Arg Arg Leu Tyr Leu Pro Asp Ile Asn
            820                 825                 830

Ser Ser Asn Ala Met Arg Arg Lys Gly Ala Glu Arg Val Ala Ile Asn
            835                 840                 845

Ala Pro Met Gln Gly Thr Ala Ala Asp Ile Ile Lys Arg Ala Met Ile
850                 855                 860

Lys Leu Asp Glu Val Ile Arg His Asp Pro Asp Ile Glu Met Ile Met
865                 870                 875                 880

Gln Val His Asp Glu Leu Val Phe Glu Val Arg Ser Glu Lys Val Ala
            885                 890                 895

Phe Phe Arg Glu Gln Ile Lys Gln His Met Glu Ala Ala Ala Glu Leu
            900                 905                 910

Val Val Pro Leu Ile Val Glu Val Gly Val Gly Gln Asn Trp Asp Glu
            915                 920                 925

Ala His
    930

<210> SEQ ID NO 6
<211> LENGTH: 904
<212> TYPE: PRT
<213> ORGANISM: Mycobacterium tuberculosis

<400> SEQUENCE: 6

Met Val Thr Thr Ala Ser Ala Pro Ser Glu Asp Arg Ala Lys Pro Thr
1               5                   10                  15

Leu Met Leu Leu Asp Gly Asn Ser Leu Ala Phe Arg Ala Phe Tyr Ala
            20                  25                  30

Leu Pro Ala Glu Asn Phe Lys Thr Arg Gly Gly Leu Thr Thr Asn Ala
            35                  40                  45

Val Tyr Gly Phe Thr Ala Met Leu Ile Asn Leu Leu Arg Asp Glu Ala
            50                  55                  60

Pro Thr His Ile Ala Ala Ala Phe Asp Val Ser Arg Gln Thr Phe Arg

-continued

```
                65                  70                  75                  80
Leu Gln Arg Tyr Pro Glu Tyr Lys Ala Asn Arg Ser Ser Thr Pro Asp
                85                  90                  95
Glu Phe Ala Gly Gln Ile Asp Ile Thr Lys Glu Val Leu Gly Ala Leu
               100                 105                 110
Gly Ile Thr Val Leu Ser Glu Pro Gly Phe Glu Ala Asp Asp Leu Ile
               115                 120                 125
Ala Thr Leu Ala Thr Gln Ala Glu Asn Glu Gly Tyr Arg Val Leu Val
               130                 135                 140
Val Thr Gly Asp Arg Asp Ala Leu Gln Leu Val Ser Asp Asp Val Thr
145                150                 155                 160
Val Leu Tyr Pro Arg Lys Gly Val Ser Glu Leu Thr Arg Phe Thr Pro
               165                 170                 175
Glu Ala Val Val Glu Lys Tyr Gly Leu Thr Pro Arg Gln Tyr Pro Asp
               180                 185                 190
Phe Ala Ala Leu Arg Gly Asp Pro Ser Asp Asn Leu Pro Gly Ile Pro
               195                 200                 205
Gly Val Gly Glu Lys Thr Ala Ala Lys Trp Ile Ala Glu Tyr Gly Ser
210                215                 220
Leu Arg Ser Leu Val Asp Asn Val Asp Ala Val Arg Gly Lys Val Gly
225                230                 235                 240
Asp Ala Leu Arg Ala Asn Leu Ala Ser Val Val Arg Asn Arg Glu Leu
               245                 250                 255
Thr Asp Leu Val Arg Asp Val Pro Leu Ala Gln Thr Pro Asp Thr Leu
               260                 265                 270
Arg Leu Gln Pro Trp Asp Arg Asp His Ile His Arg Leu Phe Asp Asp
               275                 280                 285
Leu Glu Phe Arg Val Leu Arg Asp Arg Leu Phe Asp Thr Leu Ala Ala
               290                 295                 300
Ala Gly Gly Pro Glu Val Asp Glu Gly Phe Asp Val Arg Gly Gly Ala
305                310                 315                 320
Leu Ala Pro Gly Thr Val Arg Gln Trp Leu Ala Glu His Ala Gly Asp
               325                 330                 335
Gly Arg Arg Ala Gly Leu Thr Val Val Gly Thr His Leu Pro His Gly
               340                 345                 350
Gly Asp Ala Thr Ala Met Ala Val Ala Ala Asp Gly Glu Gly Ala
               355                 360                 365
Tyr Leu Asp Thr Ala Thr Leu Thr Pro Asp Asp Ala Ala Leu Ala
               370                 375                 380
Ala Trp Leu Ala Asp Pro Ala Lys Pro Lys Ala Leu His Glu Ala Lys
385                390                 395                 400
Ala Ala Val His Asp Leu Ala Gly Arg Gly Trp Thr Leu Glu Gly Val
               405                 410                 415
Thr Ser Asp Thr Ala Leu Ala Ala Tyr Leu Val Arg Pro Gly Gln Arg
               420                 425                 430
Ser Phe Thr Leu Asp Asp Leu Ser Leu Arg Tyr Leu Arg Arg Glu Leu
               435                 440                 445
Arg Ala Glu Thr Pro Gln Gln Gln Leu Ser Leu Leu Asp Asp Asp
               450                 455                 460
Asp Thr Asp Ala Glu Thr Ile Gln Thr Thr Ile Leu Arg Ala Arg Ala
465                470                 475                 480
Val Ile Asp Leu Ala Asp Ala Leu Asp Ala Glu Leu Ala Arg Ile Asp
               485                 490                 495
```

-continued

Ser Thr Ala Leu Leu Gly Glu Met Glu Leu Pro Val Gln Arg Val Leu
            500                 505                 510

Ala Lys Met Glu Ser Ala Gly Ile Ala Val Asp Leu Pro Met Leu Thr
            515                 520                 525

Glu Leu Gln Ser Gln Phe Gly Asp Gln Ile Arg Asp Ala Ala Glu Ala
            530                 535                 540

Ala Tyr Gly Val Ile Gly Lys Gln Ile Asn Leu Gly Ser Pro Lys Gln
545                 550                 555                 560

Leu Gln Val Val Leu Phe Asp Glu Leu Gly Met Pro Lys Thr Lys Arg
                565                 570                 575

Thr Lys Thr Gly Tyr Thr Thr Asp Ala Asp Ala Leu Gln Ser Leu Phe
            580                 585                 590

Asp Lys Thr Gly His Pro Phe Leu Gln His Leu Leu Ala His Arg Asp
            595                 600                 605

Val Thr Arg Leu Lys Val Thr Val Asp Gly Leu Leu Gln Ala Val Ala
            610                 615                 620

Ala Asp Gly Arg Ile His Thr Thr Phe Asn Gln Thr Ile Ala Ala Thr
625                 630                 635                 640

Gly Arg Leu Ser Ser Thr Glu Pro Asn Leu Gln Asn Ile Pro Ile Arg
                645                 650                 655

Thr Asp Ala Gly Arg Arg Ile Arg Asp Ala Phe Val Val Gly Asp Gly
            660                 665                 670

Tyr Ala Glu Leu Met Thr Ala Asp Tyr Ser Gln Ile Glu Met Arg Ile
            675                 680                 685

Met Ala His Leu Ser Gly Asp Glu Gly Leu Ile Glu Ala Phe Asn Thr
            690                 695                 700

Gly Glu Asp Leu His Ser Phe Val Ala Ser Arg Ala Phe Gly Val Pro
705                 710                 715                 720

Ile Asp Glu Val Thr Gly Glu Leu Arg Arg Val Lys Ala Met Ser
                725                 730                 735

Tyr Gly Leu Ala Tyr Gly Leu Ser Ala Tyr Gly Leu Ser Gln Gln Leu
            740                 745                 750

Lys Ile Ser Thr Glu Glu Ala Asn Glu Gln Met Asp Ala Tyr Phe Ala
            755                 760                 765

Arg Phe Gly Gly Val Arg Asp Tyr Leu Arg Ala Val Val Glu Arg Ala
            770                 775                 780

Arg Lys Asp Gly Tyr Thr Ser Thr Val Leu Gly Arg Arg Tyr Leu
785                 790                 795                 800

Pro Glu Leu Asp Ser Ser Asn Arg Gln Val Arg Glu Ala Ala Glu Arg
                805                 810                 815

Ala Ala Leu Asn Ala Pro Ile Gln Gly Ser Ala Ala Asp Ile Ile Lys
            820                 825                 830

Val Ala Met Ile Gln Val Asp Lys Ala Leu Asn Glu Ala Gln Leu Ala
            835                 840                 845

Ser Arg Met Leu Leu Gln Val His Asp Glu Leu Leu Phe Glu Ile Ala
            850                 855                 860

Pro Gly Glu Arg Glu Arg Val Glu Ala Leu Val Arg Asp Lys Met Gly
865                 870                 875                 880

Gly Ala Tyr Pro Leu Asp Val Pro Leu Glu Val Ser Val Gly Tyr Gly
                885                 890                 895

Arg Ser Trp Asp Ala Ala His
            900

<210> SEQ ID NO 7
<211> LENGTH: 877
<212> TYPE: PRT
<213> ORGANISM: Streptococcus pneumoniae (strain ATCC BAA-255/R6)

<400> SEQUENCE: 7

```
Met Asp Lys Lys Lys Leu Leu Leu Ile Asp Gly Ser Ser Val Ala Phe
1               5                   10                  15

Arg Ala Phe Phe Ala Leu Tyr Gln Gln Leu Asp Arg Phe Lys Asn Ala
            20                  25                  30

Ala Gly Leu His Thr Asn Ala Ile Tyr Gly Phe Gln Leu Met Leu Ser
        35                  40                  45

His Leu Leu Glu Arg Val Glu Pro Ser His Ile Leu Val Ala Phe Asp
    50                  55                  60

Ala Gly Lys Thr Thr Phe Arg Thr Glu Met Tyr Ala Asp Tyr Lys Gly
65                  70                  75                  80

Gly Arg Ala Lys Thr Pro Asp Glu Phe Arg Glu Gln Phe Pro Phe Ile
            85                  90                  95

Arg Glu Leu Leu Asp His Met Gly Ile Arg His Tyr Glu Leu Ala Gln
            100                 105                 110

Tyr Glu Ala Asp Asp Ile Ile Gly Thr Leu Asp Lys Leu Ala Glu Gln
        115                 120                 125

Asp Gly Phe Asp Ile Thr Ile Val Ser Gly Asp Lys Asp Leu Ile Gln
    130                 135                 140

Leu Thr Asp Glu His Thr Val Val Glu Ile Ser Lys Lys Gly Val Ala
145                 150                 155                 160

Glu Phe Glu Ala Phe Thr Pro Asp Tyr Leu Met Glu Met Gly Leu
            165                 170                 175

Thr Pro Ala Gln Phe Ile Asp Leu Lys Ala Leu Met Gly Asp Lys Ser
            180                 185                 190

Asp Asn Ile Pro Gly Val Thr Lys Val Gly Glu Lys Thr Gly Ile Lys
        195                 200                 205

Leu Leu Leu Glu His Gly Ser Leu Glu Gly Ile Tyr Glu Asn Ile Asp
    210                 215                 220

Gly Met Lys Thr Ser Lys Met Lys Glu Asn Leu Ile Asn Asp Lys Glu
225                 230                 235                 240

Gln Ala Phe Leu Ser Lys Thr Leu Ala Thr Ile Asp Thr Lys Ala Pro
            245                 250                 255

Ile Ala Ile Gly Leu Glu Asp Leu Val Tyr Ser Gly Pro Asp Val Glu
            260                 265                 270

Asn Leu Gly Lys Phe Tyr Asp Glu Met Gly Phe Lys Gln Leu Lys Gln
        275                 280                 285

Ala Leu Asn Met Ser Ser Ala Asp Val Ala Glu Gly Leu Asp Phe Thr
    290                 295                 300

Ile Val Asp Gln Ile Ser Gln Asp Met Leu Ser Glu Ser Ile Phe
305                 310                 315                 320

His Phe Glu Leu Phe Gly Glu Asn Tyr His Thr Asp Asn Leu Val Gly
            325                 330                 335

Phe Ala Trp Ser Cys Gly Asp Gln Leu Tyr Ala Thr Lys Leu Glu
            340                 345                 350

Leu Leu Gln Asp Pro Ile Phe Lys Asp Phe Leu Glu Lys Thr Ser Leu
        355                 360                 365

Arg Val Tyr Asp Phe Lys Lys Val Lys Val Leu Leu Gln Arg Phe Gly
    370                 375                 380
```

```
Val Asp Leu Gln Ala Pro Ala Phe Asp Ile Arg Leu Ala Lys Tyr Leu
385                 390                 395                 400

Leu Ser Thr Val Glu Asp Asn Glu Ile Ala Thr Ile Ala Ser Leu Tyr
            405                 410                 415

Gly Gln Thr Tyr Leu Val Asp Asp Glu Thr Phe Tyr Gly Lys Gly Val
        420                 425                 430

Lys Lys Ala Ile Pro Glu Arg Glu Lys Phe Leu Glu His Leu Ala Cys
        435                 440                 445

Lys Leu Ala Val Leu Val Glu Thr Glu Pro Ile Leu Leu Glu Lys Leu
    450                 455                 460

Ser Glu Asn Gly Gln Leu Glu Leu Leu Tyr Asp Met Glu Gln Pro Leu
465                 470                 475                 480

Ala Phe Val Leu Ala Lys Met Glu Ile Ala Gly Ile Val Lys Lys
            485                 490                 495

Glu Thr Leu Leu Glu Met Gln Ala Glu Asn Glu Leu Val Ile Glu Lys
            500                 505                 510

Leu Thr Gln Glu Ile Tyr Glu Leu Ala Gly Glu Glu Phe Asn Val Asn
        515                 520                 525

Ser Pro Lys Gln Leu Gly Val Leu Leu Phe Glu Lys Leu Gly Leu Pro
530                 535                 540

Leu Glu Tyr Thr Lys Lys Thr Lys Thr Gly Tyr Ser Thr Ala Val Asp
545                 550                 555                 560

Val Leu Glu Arg Leu Ala Pro Ile Ala Pro Ile Val Lys Lys Ile Leu
            565                 570                 575

Asp Tyr Arg Gln Ile Ala Lys Ile Gln Ser Thr Tyr Val Ile Gly Leu
        580                 585                 590

Gln Asp Trp Ile Leu Ala Asp Gly Lys Ile His Thr Arg Tyr Val Gln
        595                 600                 605

Asp Leu Thr Gln Thr Gly Arg Leu Ser Ser Val Asp Pro Asn Leu Gln
        610                 615                 620

Asn Ile Pro Ala Arg Leu Glu Gln Gly Arg Leu Ile Arg Lys Ala Phe
625                 630                 635                 640

Val Pro Glu Trp Glu Asp Ser Val Leu Leu Ser Ser Asp Tyr Ser Gln
            645                 650                 655

Ile Glu Leu Arg Val Leu Ala His Ile Ser Lys Asp Glu His Leu Ile
            660                 665                 670

Lys Ala Phe Gln Glu Gly Ala Asp Ile His Thr Ser Thr Ala Met Arg
        675                 680                 685

Val Phe Gly Ile Glu Arg Pro Asp Asn Val Thr Ala Asn Asp Arg Arg
        690                 695                 700

Asn Ala Lys Ala Val Asn Phe Gly Val Val Tyr Gly Ile Ser Asp Phe
705                 710                 715                 720

Gly Leu Ser Asn Asn Leu Gly Ile Ser Arg Lys Glu Ala Lys Ala Tyr
            725                 730                 735

Ile Asp Thr Tyr Phe Glu Arg Phe Pro Gly Ile Lys Asn Tyr Met Asp
        740                 745                 750

Glu Val Val Arg Glu Ala Arg Asp Lys Gly Tyr Val Glu Thr Leu Phe
        755                 760                 765

Lys Arg Arg Arg Glu Leu Pro Asp Ile Asn Ser Arg Asn Phe Asn Ile
    770                 775                 780

Arg Gly Phe Ala Glu Arg Thr Ala Ile Asn Ser Pro Ile Gln Gly Ser
785                 790                 795                 800
```

```
Ala Ala Asp Ile Leu Lys Ile Ala Met Ile Gln Leu Asp Lys Ala Leu
                805                 810                 815

Val Ala Gly Gly Tyr Gln Thr Lys Met Leu Leu Gln Val His Asp Glu
            820                 825                 830

Ile Val Leu Glu Val Pro Lys Ser Glu Leu Val Glu Met Lys Lys Leu
                835                 840                 845

Val Lys Gln Thr Met Glu Glu Ala Ile Gln Leu Ser Val Pro Leu Ile
850                 855                 860

Ala Asp Glu Asn Glu Gly Ala Thr Trp Tyr Glu Ala Lys
865                 870                 875

<210> SEQ ID NO 8
<211> LENGTH: 1254
<212> TYPE: PRT
<213> ORGANISM: Saccharomyces cerevisiae

<400> SEQUENCE: 8

Met Thr Lys Leu Met Val Arg Ser Glu Cys Met Leu Arg Met Val Arg
1               5                   10                  15

Arg Arg Pro Leu Arg Val Gln Phe Cys Ala Arg Trp Phe Ser Thr Lys
            20                  25                  30

Lys Asn Thr Ala Glu Ala Pro Arg Ile Asn Pro Val Gly Ile Gln Tyr
        35                  40                  45

Leu Gly Glu Ser Leu Gln Arg Gln Val Phe Gly Ser Cys Gly Gly Lys
    50                  55                  60

Asp Glu Val Glu Gln Ser Asp Lys Leu Met Glu Leu Ser Lys Lys Ser
65                  70                  75                  80

Leu Lys Asp His Gly Leu Trp Gly Lys Lys Thr Leu Ile Thr Asp Pro
                85                  90                  95

Ile Ser Phe Pro Leu Pro Pro Leu Gln Gly Arg Ser Leu Asp Glu His
            100                 105                 110

Phe Gln Lys Ile Gly Arg Phe Asn Ser Glu Pro Tyr Lys Ser Phe Cys
        115                 120                 125

Glu Asp Lys Phe Thr Glu Met Val Ala Arg Pro Ala Glu Trp Leu Arg
130                 135                 140

Lys Pro Gly Trp Val Lys Tyr Val Pro Gly Met Ala Pro Val Glu Val
145                 150                 155                 160

Ala Tyr Pro Asp Glu Glu Leu Val Val Phe Asp Val Gly Thr Leu Tyr
                165                 170                 175

Asn Val Ser Asp Tyr Pro Thr Leu Ala Thr Ala Leu Ser Ser Thr Ala
            180                 185                 190

Trp Tyr Leu Trp Cys Ser Pro Phe Ile Cys Gly Gly Asp Asp Pro Ala
        195                 200                 205

Ala Leu Ile Pro Leu Asn Thr Leu Asn Lys Glu Gln Val Ile Ile Gly
    210                 215                 220

His Asn Val Ala Tyr Asp Arg Ala Arg Val Leu Glu Glu Tyr Asn Phe
225                 230                 235                 240

Arg Asp Ser Lys Ala Phe Phe Leu Asp Thr Gln Ser Leu His Ile Ala
                245                 250                 255

Ser Phe Gly Leu Cys Ser Arg Gln Arg Pro Met Phe Met Lys Asn Asn
            260                 265                 270

Lys Lys Lys Glu Ala Glu Val Glu Ser Glu Val His Pro Glu Ile Ser
        275                 280                 285

Ile Glu Asp Tyr Asp Asp Pro Trp Leu Asn Val Ser Ala Leu Asn Ser
    290                 295                 300
```

```
Leu Lys Asp Val Ala Lys Phe His Cys Lys Ile Asp Leu Asp Lys Thr
305                 310                 315                 320

Asp Arg Asp Phe Phe Ala Ser Thr Asp Lys Ser Thr Ile Ile Glu Asn
                    325                 330                 335

Phe Gln Lys Leu Val Asn Tyr Cys Ala Thr Asp Val Thr Ala Thr Ser
            340                 345                 350

Gln Val Phe Asp Glu Ile Phe Pro Val Phe Leu Lys Lys Cys Pro His
                355                 360                 365

Pro Val Ser Phe Ala Gly Leu Lys Ser Leu Ser Lys Cys Ile Leu Pro
            370                 375                 380

Thr Lys Leu Asn Asp Trp Asn Asp Tyr Leu Asn Ser Ser Glu Ser Leu
385                 390                 395                 400

Tyr Gln Gln Ser Lys Val Gln Ile Glu Ser Lys Ile Val Gln Ile Ile
                405                 410                 415

Lys Asp Ile Val Leu Leu Lys Asp Lys Pro Asp Phe Tyr Leu Lys Asp
            420                 425                 430

Pro Trp Leu Ser Gln Leu Asp Trp Thr Thr Lys Pro Leu Arg Leu Thr
                435                 440                 445

Lys Lys Gly Val Pro Ala Lys Cys Gln Lys Leu Pro Gly Phe Pro Glu
            450                 455                 460

Trp Tyr Arg Gln Leu Phe Pro Ser Lys Asp Thr Val Glu Pro Lys Ile
465                 470                 475                 480

Thr Ile Lys Ser Arg Ile Ile Pro Ile Leu Phe Lys Leu Ser Trp Glu
                485                 490                 495

Asn Ser Pro Val Ile Trp Ser Lys Glu Ser Gly Trp Cys Phe Asn Val
            500                 505                 510

Pro His Glu Gln Val Glu Thr Tyr Lys Ala Lys Asn Tyr Val Leu Ala
            515                 520                 525

Asp Ser Val Ser Gln Glu Glu Glu Ile Arg Thr His Asn Leu Gly
    530                 535                 540

Leu Gln Cys Thr Gly Val Leu Phe Lys Val Pro His Pro Asn Gly Pro
545                 550                 555                 560

Thr Phe Asn Cys Thr Asn Leu Leu Thr Lys Ser Tyr Asn His Phe Phe
                565                 570                 575

Glu Lys Gly Val Leu Lys Ser Glu Ser Glu Leu Ala His Gln Ala Leu
            580                 585                 590

Gln Ile Asn Ser Ser Gly Ser Tyr Trp Met Ser Ala Arg Glu Arg Ile
                595                 600                 605

Gln Ser Gln Phe Val Val Pro Ser Cys Lys Phe Pro Asn Glu Phe Gln
            610                 615                 620

Ser Leu Ser Ala Lys Ser Leu Asn Asn Glu Lys Thr Asn Asp Leu
625                 630                 635                 640

Ala Ile Ile Ile Pro Lys Ile Val Pro Met Gly Thr Ile Thr Arg Arg
                645                 650                 655

Ala Val Glu Asn Ala Trp Leu Thr Ala Ser Asn Ala Lys Ala Asn Arg
            660                 665                 670

Ile Gly Ser Glu Leu Lys Thr Gln Val Lys Ala Pro Pro Gly Tyr Cys
                675                 680                 685

Phe Val Gly Ala Asp Val Asp Ser Glu Glu Leu Trp Ile Ala Ser Leu
            690                 695                 700

Val Gly Asp Ser Ile Phe Asn Val His Gly Gly Thr Ala Ile Gly Trp
705                 710                 715                 720
```

-continued

Met Cys Leu Glu Gly Thr Lys Asn Glu Gly Thr Asp Leu His Thr Lys
             725                 730                 735

Thr Ala Gln Ile Leu Gly Cys Ser Arg Asn Glu Ala Lys Ile Phe Asn
         740                 745                 750

Tyr Gly Arg Ile Tyr Gly Ala Gly Ala Lys Phe Ala Ser Gln Leu Leu
     755                 760                 765

Lys Arg Phe Asn Pro Ser Leu Thr Asp Glu Glu Thr Lys Lys Ile Ala
770                 775                 780

Asn Lys Leu Tyr Glu Asn Thr Lys Gly Lys Thr Lys Arg Ser Lys Leu
785                 790                 795                 800

Phe Lys Lys Phe Trp Tyr Gly Gly Ser Glu Ser Ile Leu Phe Asn Lys
                 805                 810                 815

Leu Glu Ser Ile Ala Glu Gln Glu Thr Pro Lys Thr Pro Val Leu Gly
             820                 825                 830

Cys Gly Ile Thr Tyr Ser Leu Met Lys Lys Asn Leu Arg Ala Asn Ser
         835                 840                 845

Phe Leu Pro Ser Arg Ile Asn Trp Ala Ile Gln Ser Ser Gly Val Asp
     850                 855                 860

Tyr Leu His Leu Leu Cys Cys Ser Met Glu Tyr Ile Ile Lys Lys Tyr
865                 870                 875                 880

Asn Leu Glu Ala Arg Leu Cys Ile Ser Ile His Asp Glu Ile Arg Phe
                 885                 890                 895

Leu Val Ser Glu Lys Asp Lys Tyr Arg Ala Ala Met Ala Leu Gln Ile
             900                 905                 910

Ser Asn Ile Trp Thr Arg Ala Met Phe Cys Gln Gln Met Gly Ile Asn
         915                 920                 925

Glu Leu Pro Gln Asn Cys Ala Phe Phe Ser Gln Val Asp Ile Asp Ser
     930                 935                 940

Val Ile Arg Lys Glu Val Asn Met Asp Cys Ile Thr Pro Ser Asn Lys
945                 950                 955                 960

Thr Ala Ile Pro His Gly Glu Ala Leu Asp Ile Asn Gln Leu Leu Asp
                 965                 970                 975

Lys Ser Asn Ser Lys Leu Gly Lys Pro Asn Leu Asp Ile Asp Ser Lys
             980                 985                 990

Val Ser Gln Tyr Ala Tyr Asn Tyr Arg Glu Pro Val Phe Glu Glu Tyr
         995                 1000                1005

Asn Lys Ser Tyr Thr Pro Glu Phe Leu Lys Tyr Phe Leu Ala Met Gln
     1010                1015                1020

Val Gln Ser Asp Lys Arg Asp Val Asn Arg Leu Glu Asp Glu Tyr Leu
1025                1030                1035                1040

Arg Glu Cys Thr Ser Lys Glu Tyr Ala Arg Asp Gly Asn Thr Ala Glu
                 1045                1050                1055

Tyr Ser Leu Leu Asp Tyr Ile Lys Asp Val Glu Lys Gly Lys Arg Thr
             1060                1065                1070

Lys Val Arg Ile Met Gly Ser Asn Phe Leu Asp Gly Thr Lys Asn Ala
         1075                1080                1085

Lys Ala Asp Gln Arg Ile Arg Leu Pro Val Asn Met Pro Asp Tyr Pro
     1090                1095                1100

Thr Leu His Lys Ile Ala Asn Asp Ser Ala Ile Pro Glu Lys Gln Leu
1105                1110                1115                1120

Leu Glu Asn Arg Arg Lys Lys Glu Asn Arg Ile Asp Asp Glu Asn Lys
                 1125                1130                1135

Lys Lys Leu Thr Arg Lys Lys Asn Thr Thr Pro Met Glu Arg Lys Tyr

```
                  1140              1145              1150

Lys Arg Val Tyr Gly Arg Lys Ala Phe Glu Ala Phe Tyr Glu Cys
            1155              1160              1165

Ala Asn Lys Pro Leu Asp Tyr Thr Leu Glu Thr Glu Lys Gln Phe Phe
    1170              1175              1180

Asn Ile Pro Ile Asp Gly Val Ile Asp Val Leu Asn Asp Lys Ser
1185              1190              1195              1200

Asn Tyr Lys Lys Lys Pro Ser Gln Ala Arg Thr Ala Ser Ser Pro
            1205              1210              1215

Ile Arg Lys Thr Ala Lys Ala Val His Ser Lys Lys Leu Pro Ala Arg
            1220              1225              1230

Lys Ser Ser Thr Thr Asn Arg Asn Leu Val Glu Leu Glu Arg Asp Ile
        1235              1240              1245

Thr Ile Ser Arg Glu Tyr
        1250

<210> SEQ ID NO 9
<211> LENGTH: 1239
<212> TYPE: PRT
<213> ORGANISM: Homo sapiens

<400> SEQUENCE: 9

Met Ser Arg Leu Leu Trp Arg Lys Val Ala Gly Ala Thr Val Gly Pro
1               5                   10                  15

Gly Pro Val Pro Ala Pro Gly Arg Trp Val Ser Ser Val Pro Ala
                20                  25                  30

Ser Asp Pro Ser Asp Gly Gln Arg Arg Gln Gln Gln Gln Gln
            35                  40                  45

Gln Gln Gln Gln Gln Gln Pro Gln Gln Pro Gln Val Leu Ser Ser
    50                  55                  60

Glu Gly Gly Gln Leu Arg His Asn Pro Leu Asp Ile Gln Met Leu Ser
65                  70                  75                  80

Arg Gly Leu His Glu Gln Ile Phe Gly Gln Gly Glu Met Pro Gly
                85                  90                  95

Glu Ala Ala Val Arg Arg Ser Glu His Leu Gln Lys His Gly Leu
            100                 105                 110

Trp Gly Gln Pro Ala Val Pro Leu Pro Asp Val Glu Leu Arg Leu Pro
        115                 120                 125

Pro Leu Tyr Gly Asp Asn Leu Asp Gln His Phe Arg Leu Leu Ala Gln
    130                 135                 140

Lys Gln Ser Leu Pro Tyr Leu Glu Ala Ala Asn Leu Leu Leu Gln Ala
145                 150                 155                 160

Gln Leu Pro Pro Lys Pro Pro Ala Trp Ala Trp Ala Glu Gly Trp Thr
                165                 170                 175

Arg Tyr Gly Pro Glu Gly Glu Ala Val Pro Val Ala Ile Pro Glu Glu
            180                 185                 190

Arg Ala Leu Val Phe Asp Val Glu Val Cys Leu Ala Glu Gly Thr Cys
        195                 200                 205

Pro Thr Leu Ala Val Ala Ile Ser Pro Ser Ala Trp Tyr Ser Trp Cys
    210                 215                 220

Ser Gln Arg Leu Val Glu Glu Arg Tyr Ser Trp Thr Ser Gln Leu Ser
225                 230                 235                 240

Pro Ala Asp Leu Ile Pro Leu Glu Val Pro Thr Gly Ala Ser Ser Pro
                245                 250                 255
```

```
Thr Gln Arg Asp Trp Gln Glu Gln Leu Val Val Gly His Asn Val Ser
            260                 265                 270

Phe Asp Arg Ala His Ile Arg Glu Gln Tyr Leu Ile Gln Gly Ser Arg
            275                 280                 285

Met Arg Phe Leu Asp Thr Met Ser Met His Met Ala Ile Ser Gly Leu
        290                 295                 300

Ser Ser Phe Gln Arg Ser Leu Trp Ile Ala Ala Lys Gln Gly Lys His
305                 310                 315                 320

Lys Val Gln Pro Pro Thr Lys Gln Gly Gln Lys Ser Gln Arg Lys Ala
                325                 330                 335

Arg Arg Gly Pro Ala Ile Ser Ser Trp Asp Trp Leu Asp Ile Ser Ser
            340                 345                 350

Val Asn Ser Leu Ala Glu Val His Arg Leu Tyr Val Gly Gly Pro Pro
        355                 360                 365

Leu Glu Lys Glu Pro Arg Glu Leu Phe Val Lys Gly Thr Met Lys Asp
        370                 375                 380

Ile Arg Glu Asn Phe Gln Asp Leu Met Gln Tyr Cys Ala Gln Asp Val
385                 390                 395                 400

Trp Ala Thr His Glu Val Phe Gln Gln Gln Leu Pro Leu Phe Leu Glu
                405                 410                 415

Arg Cys Pro His Pro Val Thr Leu Ala Gly Met Leu Glu Met Gly Val
            420                 425                 430

Ser Tyr Leu Pro Val Asn Gln Asn Trp Glu Arg Tyr Leu Ala Glu Ala
        435                 440                 445

Gln Gly Thr Tyr Glu Glu Leu Gln Arg Glu Met Lys Lys Ser Leu Met
        450                 455                 460

Asp Leu Ala Asn Asp Ala Cys Gln Leu Leu Ser Gly Glu Arg Tyr Lys
465                 470                 475                 480

Glu Asp Pro Trp Leu Trp Asp Leu Glu Trp Asp Leu Gln Glu Phe Lys
                485                 490                 495

Gln Lys Lys Ala Lys Lys Val Lys Lys Glu Pro Ala Thr Ala Ser Lys
            500                 505                 510

Leu Pro Ile Glu Gly Ala Gly Ala Pro Gly Asp Pro Met Asp Gln Glu
        515                 520                 525

Asp Leu Gly Pro Cys Ser Glu Glu Glu Phe Gln Gln Asp Val Met
        530                 535                 540

Ala Arg Ala Cys Leu Gln Lys Leu Lys Gly Thr Thr Glu Leu Leu Pro
545                 550                 555                 560

Lys Arg Pro Gln His Leu Pro Gly His Pro Gly Trp Tyr Arg Lys Leu
                565                 570                 575

Cys Pro Arg Leu Asp Asp Pro Ala Trp Thr Pro Gly Pro Ser Leu Leu
            580                 585                 590

Ser Leu Gln Met Arg Val Thr Pro Lys Leu Met Ala Leu Thr Trp Asp
        595                 600                 605

Gly Phe Pro Leu His Tyr Ser Glu Arg His Gly Trp Gly Tyr Leu Val
        610                 615                 620

Pro Gly Arg Arg Asp Asn Leu Ala Lys Leu Pro Thr Gly Thr Leu
625                 630                 635                 640

Glu Ser Ala Gly Val Val Cys Pro Tyr Arg Ala Ile Glu Ser Leu Tyr
                645                 650                 655

Arg Lys His Cys Leu Glu Gln Gly Lys Gln Gln Leu Met Pro Gln Glu
            660                 665                 670

Ala Gly Leu Ala Glu Glu Phe Leu Leu Thr Asp Asn Ser Ala Ile Trp
```

-continued

```
            675                 680                 685
Gln Thr Val Glu Glu Leu Asp Tyr Leu Glu Val Glu Ala Glu Ala Lys
            690                 695                 700
Met Glu Asn Leu Arg Ala Ala Val Pro Gly Gln Pro Leu Ala Leu Thr
705                 710                 715                 720
Ala Arg Gly Gly Pro Lys Asp Thr Gln Pro Ser Tyr His His Gly Asn
                    725                 730                 735
Gly Pro Tyr Asn Asp Val Asp Ile Pro Gly Cys Trp Phe Phe Lys Leu
                    740                 745                 750
Pro His Lys Asp Gly Asn Ser Cys Asn Val Gly Ser Pro Phe Ala Lys
                    755                 760                 765
Asp Phe Leu Pro Lys Met Glu Asp Gly Thr Leu Gln Ala Gly Pro Gly
                    770                 775                 780
Gly Ala Ser Gly Pro Arg Ala Leu Glu Ile Asn Lys Met Ile Ser Phe
785                 790                 795                 800
Trp Arg Asn Ala His Lys Arg Ile Ser Ser Gln Met Val Val Trp Leu
                    805                 810                 815
Pro Arg Ser Ala Leu Pro Arg Ala Val Ile Arg His Pro Asp Tyr Asp
                    820                 825                 830
Glu Glu Gly Leu Tyr Gly Ala Ile Leu Pro Gln Val Thr Ala Gly
                    835                 840                 845
Thr Ile Thr Arg Arg Ala Val Glu Pro Thr Trp Leu Thr Ala Ser Asn
            850                 855                 860
Ala Arg Pro Asp Arg Val Gly Ser Glu Leu Lys Ala Met Val Gln Ala
865                 870                 875                 880
Pro Pro Gly Tyr Thr Leu Val Gly Ala Asp Val Asp Ser Gln Glu Leu
                    885                 890                 895
Trp Ile Ala Ala Val Leu Gly Asp Ala His Phe Ala Gly Met His Gly
                    900                 905                 910
Cys Thr Ala Phe Gly Trp Met Thr Leu Gln Gly Arg Lys Ser Arg Gly
                    915                 920                 925
Thr Asp Leu His Ser Lys Thr Ala Thr Thr Val Gly Ile Ser Arg Glu
            930                 935                 940
His Ala Lys Ile Phe Asn Tyr Gly Arg Ile Tyr Gly Ala Gly Gln Pro
945                 950                 955                 960
Phe Ala Glu Arg Leu Leu Met Gln Phe Asn His Arg Leu Thr Gln Gln
                    965                 970                 975
Glu Ala Ala Glu Lys Ala Gln Gln Met Tyr Ala Ala Thr Lys Gly Leu
                    980                 985                 990
Arg Trp Tyr Arg Leu Ser Asp Glu Gly Glu Trp Leu Val Arg Glu Leu
                    995                1000                1005
Asn Leu Pro Val Asp Arg Thr Glu Gly Gly Trp Ile Ser Leu Gln Asp
            1010                1015                1020
Leu Arg Lys Val Gln Arg Glu Thr Ala Arg Lys Ser Gln Trp Lys Lys
            1025                1030                1035                1040
Trp Glu Val Val Ala Glu Arg Ala Trp Lys Gly Gly Thr Glu Ser Glu
                    1045                1050                1055
Met Phe Asn Lys Leu Glu Ser Ile Ala Thr Ser Asp Ile Pro Arg Thr
                    1060                1065                1070
Pro Val Leu Gly Cys Cys Ile Ser Arg Ala Leu Glu Pro Ser Ala Val
            1075                1080                1085
Gln Glu Glu Phe Met Thr Ser Arg Val Asn Trp Val Val Gln Ser Ser
            1090                1095                1100
```

```
Ala Val Asp Tyr Leu His Leu Met Leu Val Ala Met Lys Trp Leu Phe
1105                1110                1115                1120

Glu Glu Phe Ala Ile Asp Gly Arg Phe Cys Ile Ser Ile His Asp Glu
            1125                1130                1135

Val Arg Tyr Leu Val Arg Glu Glu Asp Arg Tyr Arg Ala Ala Leu Ala
        1140                1145                1150

Leu Gln Ile Thr Asn Leu Leu Thr Arg Cys Met Phe Ala Tyr Lys Leu
        1155                1160                1165

Gly Leu Asn Asp Leu Pro Gln Ser Val Ala Phe Phe Ser Ala Val Asp
    1170                1175                1180

Ile Asp Arg Cys Leu Arg Lys Glu Val Thr Met Asp Cys Lys Thr Pro
1185                1190                1195                1200

Ser Asn Pro Thr Gly Met Glu Arg Arg Tyr Gly Ile Pro Gln Gly Glu
            1205                1210                1215

Ala Leu Asp Ile Tyr Gln Ile Ile Glu Leu Thr Lys Gly Ser Leu Glu
        1220                1225                1230

Lys Arg Ser Gln Pro Gly Pro
        1235

<210> SEQ ID NO 10
<211> LENGTH: 595
<212> TYPE: PRT
<213> ORGANISM: Mycobacteriophage L5

<400> SEQUENCE: 10

Met Ile Glu Leu Arg His Glu Val Gln Gly Asp Leu Val Thr Val Asn
1               5                   10                  15

Val Val Glu Thr Pro Glu Asp Leu Glu Gly Phe Arg Asn Phe Ile Arg
            20                  25                  30

Ala His Leu Asn Cys Leu Ala Val Asp Thr Glu Thr Thr Gly Leu Asp
        35                  40                  45

Ile Tyr Ser Asp Thr Phe Glu Cys Arg Leu Val Gln Phe Gly Thr Gln
    50                  55                  60

Asp Glu Ala Trp Val Val Pro Val Glu Leu Gly Asp Val Phe Ile Glu
65                  70                  75                  80

Asp Val Arg Ile Ala Ile Gly Ala Leu Lys Arg Met Val Leu Gln Asn
                85                  90                  95

Ala Ser Phe Asp Leu Gln Val Leu Asp Gln Cys Phe Gly Ile Glu Met
            100                 105                 110

Glu Gly Leu Trp Pro Arg Val Leu Asp Thr Gln Ile Leu Ala Lys Leu
        115                 120                 125

Val Asp Pro Arg Pro Phe Glu Ala Gly Gly Phe Gly His Ser Leu Glu
    130                 135                 140

Glu Leu Ile Ala Lys Phe Ile Ser Glu Asp Gln Ala Glu Asn Val Lys
145                 150                 155                 160

Lys Leu Met Ala Lys Leu Ala Ala Glu His Lys Thr Thr Lys Ala Lys
                165                 170                 175

Ile Trp Ser Thr Ile Asp Leu Phe His Pro Glu Tyr Leu Leu Tyr Ala
            180                 185                 190

Gly Met Asp Thr Ile Phe Thr Ala Arg Val Cys Lys Ser Leu Thr Pro
        195                 200                 205

Leu Val Pro Asp Val Ser Arg Ser Leu Val Pro Tyr Glu His Lys Ile
    210                 215                 220

Ser Glu Ile Cys Ser Tyr Ile Asp Arg Gln Gly Phe Leu Leu Asp Val
```

225                 230                 235                 240
Glu Tyr Ser Arg Ser Leu Ala Glu Lys Trp Leu Ala Asp Gln Glu Val
                245                 250                 255

Trp Glu Ala Ile Ala Phe Thr Glu Tyr Gly Val Glu Lys Val Asn Ser
            260                 265                 270

Thr Glu Asp Leu Ala Glu Gly Leu Glu Met Gly Val Lys Ile Thr
        275                 280                 285

Gly Arg Thr Glu Thr Gly Lys Arg Gln Val Asn Ala Ala Leu Leu Asp
        290                 295                 300

Lys Leu Val Glu Asp Gly Asn Glu Leu Ala Ala Ile Ala Gln Glu Ala
305                 310                 315                 320

Lys Lys Leu Gly Lys Trp Arg Lys Thr Trp Val Gln Lys Phe Ile Asp
                325                 330                 335

Thr Arg Asp Ser Glu Asp Arg Cys His Thr Phe Ile Asn Pro Leu Gln
            340                 345                 350

Ala Arg Thr Ser Arg Met Ser Ile Thr Gly Ile Pro Ala Gln Thr Leu
        355                 360                 365

Pro Ser Ser Asp Trp Ile Val Arg Arg Cys Phe Ile Ala Glu Pro Gly
    370                 375                 380

Asp Val Met Ala Ser Val Asp Tyr Gln Ala Gln Glu Leu Arg Val Leu
385                 390                 395                 400

Ala Ala Leu Ser Gly Asp Arg Asn Met Ile Glu Ala Phe Glu Asn Gly
                405                 410                 415

Ala Asp Leu His Gln Met Thr Ala Asp Ala Ala Gln Val Pro Arg Lys
            420                 425                 430

Val Gly Lys Thr Ala Asn Phe Gln Lys Val Tyr Gly Gly Ala Lys
        435                 440                 445

Ala Leu Ala Glu Ala Val Gly Ile Ser Ile Pro Val Ala Lys Arg Val
        450                 455                 460

His Glu Ala Phe Ser Ala Thr Tyr Pro Gly Val Glu Arg Leu Ser Lys
465                 470                 475                 480

Lys Leu Ala Met Glu Ala Gly Arg Asn Gly Tyr Ile Val Asn Ala Met
                485                 490                 495

Gly Arg Arg Leu Pro Val Asp Ser Ser Arg Thr Tyr Ser Ala Leu Asn
            500                 505                 510

Tyr Met Ile Gln Ser Ser Ser Arg Asp Val Thr Cys Arg Ala Leu Ile
        515                 520                 525

Arg Leu His Glu Ala Gly Tyr Thr Pro Tyr Leu Arg Leu Pro Ile His
    530                 535                 540

Asp Glu Ile Val Ala Ser Leu Pro Ala Ser Glu Ala Glu Arg Ala Ala
545                 550                 555                 560

Ala His Ile Gly His Leu Met Gln Glu Gln Met Gly Pro Val Leu Val
                565                 570                 575

Gly Thr Asp Pro Glu Val Gly Lys Arg Ser Trp Gly Ser Leu Tyr Gly
            580                 585                 590

Ala Asp Tyr
    595

<210> SEQ ID NO 11
<211> LENGTH: 924
<212> TYPE: PRT
<213> ORGANISM: Bacillus subtilis bacteriophage SPO1

<400> SEQUENCE: 11

-continued

```
Met Gly Ser Ala Leu Asp Thr Leu Lys Glu Phe Asn Pro Lys Pro Met
 1               5                  10                 15
Lys Gly Gln Gly Ser Lys Lys Ala Arg Ile Ile Ile Val Gln Glu Asn
             20                  25                  30
Pro Phe Asp Tyr Glu Tyr Arg Lys Lys Tyr Met Thr Gly Lys Ala
             35                  40                  45
Gly Lys Leu Leu Lys Phe Gly Leu Ala Glu Val Gly Ile Asp Pro Asp
 50                  55                  60
Glu Asp Val Tyr Tyr Thr Ser Ile Val Lys Tyr Pro Thr Pro Glu Asn
 65                  70                  75                  80
Arg Leu Pro Thr Pro Asp Glu Ile Lys Glu Ser Met Asp Tyr Met Trp
                 85                  90                  95
Ala Glu Ile Glu Val Ile Asp Pro Asp Ile Ile Pro Thr Gly Asn
                 100                 105                 110
Leu Ser Leu Lys Phe Leu Thr Lys Met Thr Ala Ile Thr Lys Val Arg
             115                 120                 125
Gly Lys Leu Tyr Glu Ile Glu Gly Arg Lys Phe Phe Pro Met Ile His
             130                 135                 140
Pro Asn Thr Val Leu Lys Gln Pro Lys Tyr Gln Asp Phe Phe Ile Lys
145                 150                 155                 160
Asp Leu Glu Ile Leu Ala Ser Leu Leu Glu Gly Lys Thr Pro Lys Asn
                 165                 170                 175
Val Leu Ala Phe Thr Lys Glu Arg Arg Tyr Cys Asp Thr Phe Glu Asp
                 180                 185                 190
Ala Ile Asp Glu Ile Lys Arg Tyr Leu Glu Leu Pro Ala Gly Ser Arg
             195                 200                 205
Val Val Ile Asp Leu Glu Thr Val Lys Thr Asn Pro Phe Ile Glu Lys
 210                 215                 220
Val Thr Met Lys Lys Thr Thr Leu Glu Ala Tyr Pro Met Ser Gln Gln
225                 230                 235                 240
Pro Lys Ile Val Gly Ile Gly Leu Ser Asp Arg Ser Gly Tyr Gly Cys
             245                 250                 255
Ala Ile Pro Leu Tyr His Arg Glu Asn Leu Met Lys Gly Asn Gln Ile
             260                 265                 270
Gly Thr Ile Val Lys Phe Leu Arg Lys Leu Glu Arg Glu Asp Leu
             275                 280                 285
Glu Phe Ile Ala His Asn Gly Lys Phe Asp Ile Arg Trp Leu Arg Ala
             290                 295                 300
Ser Leu Asp Ile Tyr Leu Asp Ile Ser Ile Trp Asp Thr Met Leu Ile
305                 310                 315                 320
His Ile Ile Asp Tyr Arg Gly Glu Arg Tyr Ser Trp Ser Lys Arg Leu
                 325                 330                 335
Ala Trp Leu Glu Thr Asp Met Gly Gly Tyr Asp Asp Ala Leu Asp Gly
             340                 345                 350
Glu Lys Pro Lys Gly Glu Asp Glu Gly Asn Tyr Asp Leu Ile Pro Trp
             355                 360                 365
Asp Ile Leu Lys Val Tyr Leu Ala Asp Cys Asp Val Thr Phe Arg
             370                 375                 380
Leu Ser Glu Lys Tyr Ile Pro Leu Val Glu Glu Asn Glu Glu Lys Lys
385                 390                 395                 400
Trp Leu Trp Glu Asn Ile Met Val Pro Gly Tyr Tyr Thr Leu Leu Asp
                 405                 410                 415
Ile Glu Met Asp Gly Ile His Val Asp Arg Glu Trp Leu Glu Val Leu
```

-continued

```
                420             425             430
Arg Val Ser Tyr Glu Lys Glu Ile Ser Arg Leu Glu Asp Lys Met Arg
            435             440             445
Glu Phe Pro Glu Gly Val Ala Met Glu Arg Glu Met Arg Asp Lys Trp
450             455             460
Lys Glu Arg Val Met Ile Gly Asn Ile Lys Ser Ala Asn Arg Thr Pro
465             470             475             480
Glu Gln Gln Asp Lys Phe Lys Lys Tyr Lys Tyr Asp Pro Ser Lys
            485             490             495
Gly Gly Asp Lys Ile Asn Phe Gly Ser Thr Lys Gln Leu Gly Glu Leu
            500             505             510
Leu Phe Glu Arg Met Gly Leu Glu Thr Val Ile Phe Thr Asp Lys Gly
            515             520             525
Ala Pro Ser Thr Asn Asp Ser Leu Lys Phe Met Gly Ser Gln Ser
            530             535             540
Asp Phe Val Lys Val Leu Met Glu Phe Arg Lys Ala Asn His Leu Tyr
545             550             555             560
Asn Asn Phe Val Ser Lys Leu Ser Leu Met Ile Asp Pro Asp Asn Ile
            565             570             575
Val His Pro Ser Tyr Asn Ile His Gly Thr Val Thr Gly Arg Leu Ser
            580             585             590
Ser Asn Glu Pro Asn Ala Gln Gln Phe Pro Arg Lys Val Asn Thr Pro
            595             600             605
Thr Leu Phe Gln Tyr Asn Phe Glu Ile Lys Lys Met Phe Asn Ser Arg
            610             615             620
Phe Gly Asp Gly Gly Val Ile Val Gln Phe Asp Tyr Ser Gln Leu Glu
625             630             635             640
Leu Arg Ile Leu Val Cys Tyr Tyr Ser Arg Pro Tyr Thr Ile Asp Leu
            645             650             655
Tyr Arg Ser Gly Ala Asp Leu His Lys Ala Val Ala Ser Asp Ala Phe
            660             665             670
Gly Val Ala Ile Glu Glu Val Ser Lys Asp Gln Arg Thr Ala Ser Lys
            675             680             685
Lys Ile Gln Phe Gly Ile Val Tyr Gln Glu Ser Ala Arg Gly Leu Ser
            690             695             700
Glu Asp Leu Arg Ala Glu Gly Ile Thr Met Ser Glu Asp Glu Cys Glu
705             710             715             720
Ile Phe Ile Lys Lys Tyr Phe Lys Arg Phe Pro Lys Val Ser Lys Trp
            725             730             735
Ile Arg Asp Thr Lys Lys His Val Lys Asp Ile Ser Thr Val Lys Thr
            740             745             750
Leu Thr Gly Ala Thr Arg Asn Leu Pro Asp Ile Asp Ser Ile Asp Gln
            755             760             765
Ser Lys Ala Asn Glu Ala Glu Arg Gln Ala Val Asn Thr Pro Ile Gln
            770             775             780
Gly Thr Gly Ser Asp Cys Thr Leu Met Ser Leu Ile Leu Ile Asn Gln
785             790             795             800
Trp Leu Arg Glu Ser Gly Leu Arg Ser Arg Ile Cys Ile Thr Val His
            805             810             815
Asp Ser Ile Val Leu Asp Cys Pro Lys Asp Glu Val Leu Glu Val Ala
            820             825             830
Lys Lys Val Lys His Ile Met Glu Asn Leu Gly Glu Tyr Asn Glu Phe
            835             840             845
```

```
Tyr Lys Phe Leu Gly Asp Val Pro Ile Leu Ser Glu Met Glu Ile Gly
    850                 855                 860

Arg Asn Tyr Gly Asp Ala Phe Glu Ala Thr Ile Glu Asp Ile Glu Glu
865                 870                 875                 880

His Gly Val Asp Gly Phe Ile Glu Met Lys Glu Lys Glu Lys Leu Glu
                885                 890                 895

Lys Asp Met Lys Glu Phe Thr Lys Ile Ile Glu Asp Gly Gly Ser Ile
            900                 905                 910

Pro Asp Tyr Ala Arg Ile Tyr Trp Glu Asn Ile Ser
            915                 920

<210> SEQ ID NO 12
<211> LENGTH: 704
<212> TYPE: PRT
<213> ORGANISM: Bacteriophage T7

<400> SEQUENCE: 12

Met Ile Val Ser Asp Ile Glu Ala Asn Ala Leu Leu Glu Ser Val Thr
1               5                   10                  15

Lys Phe His Cys Gly Val Ile Tyr Asp Tyr Ser Thr Ala Glu Tyr Val
            20                  25                  30

Ser Tyr Arg Pro Ser Asp Phe Gly Ala Tyr Leu Asp Ala Leu Glu Ala
        35                  40                  45

Glu Val Ala Arg Gly Gly Leu Ile Val Phe His Asn Gly His Lys Tyr
    50                  55                  60

Asp Val Pro Ala Leu Thr Lys Leu Ala Lys Leu Gln Leu Asn Arg Glu
65                  70                  75                  80

Phe His Leu Pro Arg Glu Asn Cys Ile Asp Thr Leu Val Leu Ser Arg
                85                  90                  95

Leu Ile His Ser Asn Leu Lys Asp Thr Asp Met Gly Leu Leu Arg Ser
            100                 105                 110

Gly Lys Leu Pro Gly Lys Arg Phe Gly Ser His Ala Leu Glu Ala Trp
        115                 120                 125

Gly Tyr Arg Leu Gly Glu Met Lys Gly Glu Tyr Lys Asp Asp Phe Lys
    130                 135                 140

Arg Met Leu Glu Glu Gln Gly Glu Glu Tyr Val Asp Gly Met Glu Trp
145                 150                 155                 160

Trp Asn Phe Asn Glu Glu Met Met Asp Tyr Asn Val Gln Asp Val Val
                165                 170                 175

Val Thr Lys Ala Leu Leu Glu Lys Leu Leu Ser Asp Lys His Tyr Phe
            180                 185                 190

Pro Pro Glu Ile Asp Phe Thr Asp Val Gly Tyr Thr Thr Phe Trp Ser
        195                 200                 205

Glu Ser Leu Glu Ala Val Asp Ile Glu His Arg Ala Ala Trp Leu Leu
    210                 215                 220

Ala Lys Gln Glu Arg Asn Gly Phe Pro Phe Asp Thr Lys Ala Ile Glu
225                 230                 235                 240

Glu Leu Tyr Val Glu Leu Ala Ala Arg Arg Ser Glu Leu Leu Arg Lys
                245                 250                 255

Leu Thr Glu Thr Phe Gly Ser Trp Tyr Gln Pro Lys Gly Gly Thr Glu
            260                 265                 270

Met Phe Cys His Pro Arg Thr Gly Lys Pro Leu Pro Lys Tyr Pro Arg
        275                 280                 285

Ile Lys Thr Pro Lys Val Gly Gly Ile Phe Lys Lys Pro Lys Asn Lys
```

```
                    290                 295                 300
Ala Gln Arg Glu Gly Arg Glu Pro Cys Glu Leu Asp Thr Arg Glu Tyr
305                 310                 315                 320

Val Ala Gly Ala Pro Tyr Thr Pro Val Glu His Val Val Phe Asn Pro
                    325                 330                 335

Ser Ser Arg Asp His Ile Gln Lys Lys Leu Gln Glu Ala Gly Trp Val
                340                 345                 350

Pro Thr Lys Tyr Thr Asp Lys Gly Ala Pro Val Val Asp Asp Glu Val
                355                 360                 365

Leu Glu Gly Val Arg Val Asp Asp Pro Glu Lys Gln Ala Ala Ile Asp
                370                 375                 380

Leu Ile Lys Glu Tyr Leu Met Ile Gln Lys Arg Ile Gly Gln Ser Ala
385                 390                 395                 400

Glu Gly Asp Lys Ala Trp Leu Arg Tyr Val Ala Glu Asp Gly Lys Ile
                405                 410                 415

His Gly Ser Val Asn Pro Asn Gly Ala Val Thr Gly Arg Ala Thr His
                420                 425                 430

Ala Phe Pro Asn Leu Ala Gln Ile Pro Gly Val Arg Ser Pro Tyr Gly
                435                 440                 445

Glu Gln Cys Arg Ala Ala Phe Gly Ala Glu His His Leu Asp Gly Ile
                450                 455                 460

Thr Gly Lys Pro Trp Val Gln Ala Gly Ile Asp Ala Ser Gly Leu Glu
465                 470                 475                 480

Leu Arg Cys Leu Ala His Phe Met Ala Arg Phe Asp Asn Gly Glu Tyr
                485                 490                 495

Ala His Glu Ile Leu Asn Gly Asp Ile His Thr Lys Asn Gln Ile Ala
                500                 505                 510

Ala Glu Leu Pro Thr Arg Asp Asn Ala Lys Thr Phe Ile Tyr Gly Phe
                515                 520                 525

Leu Tyr Gly Ala Gly Asp Glu Lys Ile Gly Gln Ile Val Gly Ala Gly
                530                 535                 540

Lys Glu Arg Gly Lys Glu Leu Lys Lys Lys Phe Leu Glu Asn Thr Pro
545                 550                 555                 560

Ala Ile Ala Ala Leu Arg Glu Ser Ile Gln Gln Thr Leu Val Glu Ser
                565                 570                 575

Ser Gln Trp Val Ala Gly Glu Gln Gln Val Lys Trp Lys Arg Arg Trp
                580                 585                 590

Ile Lys Gly Leu Asp Gly Arg Lys Val His Val Arg Ser Pro His Ala
                595                 600                 605

Ala Leu Asn Thr Leu Leu Gln Ser Ala Gly Ala Leu Ile Cys Lys Leu
                610                 615                 620

Trp Ile Ile Lys Thr Glu Met Leu Val Glu Lys Gly Leu Lys His
625                 630                 635                 640

Gly Trp Asp Gly Asp Phe Ala Tyr Met Ala Trp Val His Asp Glu Ile
                645                 650                 655

Gln Val Gly Cys Arg Thr Glu Glu Ile Ala Gln Val Val Ile Glu Thr
                660                 665                 670

Ala Gln Glu Ala Met Arg Trp Val Gly Asp His Trp Asn Phe Arg Cys
                675                 680                 685

Leu Leu Asp Thr Glu Gly Lys Met Gly Pro Asn Trp Ala Ile Cys His
                690                 695                 700
```